US008558055B2

(12) United States Patent
Ostertag et al.

(10) Patent No.: US 8,558,055 B2
(45) Date of Patent: Oct. 15, 2013

(54) GENETICALLY MODIFIED RAT COMPRISING A CYTOKINE GENE DISRUPTION AND EXHIBITING A GREATER SUSCEPTIBILITY TO A CYTOKINE-MEDIATED AUTOIMMUNE AND/OR INFLAMMATORY DISEASE

(75) Inventors: Eric M. Ostertag, Lexington, KY (US); John Stuart Crawford, Lexington, KY (US)

(73) Assignee: Transposagen Biopharmaceuticals, Inc., Lexington, KY (US)

( * ) Notice: Subject to any disclaimer, the term of this patent is extended or adjusted under 35 U.S.C. 154(b) by 153 days.

(21) Appl. No.: 12/842,418

(22) Filed: Jul. 23, 2010

(65) Prior Publication Data

US 2011/0023142 A1 Jan. 27, 2011

Related U.S. Application Data

(60) Provisional application No. 61/228,369, filed on Jul. 24, 2009.

(51) Int. Cl.
*C12N 15/00* (2006.01)
*A01K 67/033* (2006.01)
*A01K 67/027* (2006.01)
*G01N 33/00* (2006.01)

(52) U.S. Cl.
USPC .................................... 800/13; 800/3; 800/25

(58) Field of Classification Search
None
See application file for complete search history.

(56) References Cited

U.S. PATENT DOCUMENTS

| | | | |
|---|---|---|---|
| 4,670,388 | A | 6/1987 | Rubin et al. |
| 4,736,866 | A | 4/1988 | Leder et al. |
| 4,870,009 | A | 9/1989 | Evans et al. |
| 4,873,191 | A | 10/1989 | Wagner et al. |
| 4,897,355 | A | 1/1990 | Eppstein et al. |
| 4,945,050 | A | 7/1990 | Sanford et al. |
| 4,959,317 | A | 9/1990 | Sauer |
| 5,719,055 | A | 2/1998 | Cooper |
| 5,792,924 | A | 8/1998 | Yoder et al. |
| 6,218,185 | B1 | 4/2001 | Shirk et al. |
| 6,225,121 | B1 | 5/2001 | Savakis et al. |
| 6,475,798 | B2 | 11/2002 | Fogarty et al. |
| 6,489,458 | B2 | 12/2002 | Hackett et al. |
| 6,962,810 | B2 | 11/2005 | Fraser et al. |
| 7,148,203 | B2 | 12/2006 | Hackett et al. |
| 2007/0209083 | A1 | 9/2007 | Thiam et al. |

FOREIGN PATENT DOCUMENTS

| | | |
|---|---|---|
| WO | WO 97/07668 | 3/1997 |
| WO | WO 97/07669 | 3/1997 |
| WO | WO 2010/124200 | 10/2010 |

OTHER PUBLICATIONS

Karray et al. Complete Loss of Fas Ligand Gene Causes Massive Lymphoproliferation and Early Death, Indicating a Residual Activity of gld Allele. Journal of Immunology, 2004, vol. 172,pp. 2118-2125.*

Kitada et al. Transposon-tagged mutagenesis in the rat. Nature Methods, 2007, vol. 4, pp. 131-133.*

Dong et al. B7-H1, a third member of the B7 family, co-stimulates T-cell proliferation and interleukin-10 secretionNature Medicine, 1999, vol. 5, pp. 1365-1369.*

Kullberg et al. *Helicobacter hepaticus* Triggers Colitis in Specific-Pathogen-Free Interleukin-10 (IL-10)-Deficient Mice through an IL-12 and Gamma Interferon-Dependent Mechanism Infection Immunity, 1998, vol. 66, pp. 5157-5166.*

Kullberg et al. *Helicobacter hepaticus*-Induced Colitis in Interleukin-10-Deficient Mice: Cytokine Requirements for the Induction and Maintenance of Intestinal Inflammation. Infection Immunity, 1998, vol. 66, pp. 5157-5166, as evidenced by Kullburg et al. Infection Immunity, 2001, vol. 69, pp. 4232-4241.*

Fields, M.L. et al, The Influence of Effector T Cells and Fas Ligand on Lupus-Associated B Cells, vol. 175(1) (Jul. 1, 2005) pp. 104-111 (Abstract).

Kitada, K. et al., "Generating mutant rats using the Sleepy beauty transposon system," Methods, vol. 49(3) (May 4, 2009) pp. 236-242 (Abstract).

Lu, B. et al., "Generation of rat mutant using a color-tagged Sleepy Beauty transposon system," Mamm. Genome., vol. 18(5) (Jun. 8, 2007) pp. 338-346 (Abstract).

Nagata, S., "Human autoimmune lymphoproliferative syndrome, a defect in the apoptosis-inducing Fas receptor: A lesson from the mouse model," J. Hum. Genet., vol. 43 (1998) pp. 2-8.

(Continued)

*Primary Examiner* — Deborah Crouch
(74) *Attorney, Agent, or Firm* — Frost Brown Todd LLC

(57) ABSTRACT

The present invention relates to the engineering of animal cells, preferably mammalian, more preferably rat, that are deficient due to the disruption of gene(s) or gene product(s) resulting in cytokine-cytokine mediated autoimmune and inflammatory disease. In another aspect, the invention relates to genetically modified rats, as well as the descendants and ancestors of such animals, which are animal models of human autoimmune and inflammatory disease and methods of their use. Specifically, the invention pertains to a genetically altered rat, or a rat cell in culture, that is defective in at least one of two alleles of a cytokine gene such as the Faslg gene, the Fas gene, etc. In one embodiment, the cytokine gene is the Faslg gene. In another embodiment, the cytokine gene is one of several known cytokine genes, such as Fas, IFNγ, TNF-α, IL-2, IL-10, and IL-12. The inactivation of at least one of these cytokine alleles results in an animal with a higher susceptibility to cytokine-cytokine mediated autoimmune and inflammatory disease induction. In one embodiment, the genetically altered animal is a rat of this type and is able to serve as a useful model for cytokine-cytokine mediated autoimmune and inflammatory disease and as a test animal for autoimmune and other studies.

47 Claims, 4 Drawing Sheets

(56) References Cited

OTHER PUBLICATIONS

Phys Gen Knockout: "Strain Report for F344-Faslg Tn sb-T2/Bart3) 2.325MCwi" (May 11, 2009) http://rgd.mcw.edu/tools/strains_view.cgi?Submit=View+Strain&id=2306875.
Smits, B.M.G. et al., "Rat genetics: the next episode," Trends in Genetics, vol. 22(4) (Apr. 2006) pp. 232-240.
Acsadi, G. et al., "Human dystrophin expression in mdx mice after intramuscular injection of DNA constructs," Nature, vol. 352, (1991) pp. 815-818.
Bagshawe, K.D., "A cytotoxic agent can be generated selectively at cancer sites," Br. J. Cancer, vol. 58 (1988) pp. 700-703.
Bagshawe, K.D., "Towards generating cytotoxic agents at cancer sites," Br. J. Cancer, vol. 60 (1989) pp. 275-281.
Battelli et al., "T lymphocyte killing by a xanthine-oxidase-containing Immunotoxin," Cancer Immunol Immunother., vol. 35 (1992) pp. 421-425.
Berghammer, A.J. et al., "A Universal Marker for Genetically Modified Insects," Nature, vol. 402 (1999) pp. 370-371.
Bessereau, J.L. et al., "Mobilization of a *Drosophila* transposon in the *Caenorhabditis elegans* germ line," Nature, vol. 413 (Sep. 2001) pp. 70-74.
Bhasin, A. et al., Characterization of a Tn5 pre-cleavage synaptic complex, J. Mol. Biol., vol. 302 (2000) pp. 49-63.
Brigham et al., "Expression of a Prokaryotic Gene in Cultured Lung Endothelial Cells after Lipofection with a Plasmid Vector," Am. J. Resp. Cell. Mol. Biol, vol. 1 (1989) pp. 95-100.
Brinster, R.L. et al., "Factors Affecting the Efficiency of Introducing Foreign DNA into Mice by Microinjecting Eggs," Proc. Nat. Acad. Sci. USA, vol. 82(13) (1985) pp. 4438-4442.
Brown, V. I. et al., "Molecular and Cellular Mechanisms of Receptor-Mediated Endocytosis," DNA and Cell Biology, vol. 10(6) (1991) pp. 399-409.
Bucheton, A. et al., "The Molecular Basis of I-R Hybrid Dysgenesis in *Drosophila melanogaster*: Identification, Cloning, and Properties of the I Factor," Cell, vol. 38 (1984) 153-163.
Burres, V. et al., "The ICESt1 element of *Streptococcus thermophilus* belongs to a large family of integrative and conjugative elements that exchange modules and change their specificity of integration," Plasmid, vol. 48.(2) (2002) pp. 77-97.
Capecchi, M.R., "Altering the Genome by Homologous Recombination," Science, vol. 244 (1989) pp. 1288-1292.
Cheng, Q. et al., "Specificity determinants for bacteriophage Hong Kong 022 integrase: analysis of mutants with relaxed core-binding specificities," Mol. Microbiol., vol. 36(2) (2000) pp. 424-436.
Claesson, M.H. et al, "Antibodies Directed Against Monomorphic and Evolutionary Conserved Self Epitopes may be Generated in 'Knock-Out' Mice. Development of Monoclonal Antibodies Directed Against Monomorphic MHC Class I Determinants," Scan. J. Immunol., vol. 40 (1994) pp. 257-254.
Cui, Z. et al., "Structure-Function Analysis of the Inverted Terminal Repeats of the Sleeping Beauty Transposon," J. Mol. Biol., vol. 318 (2002) pp. 1221-1235.
Declerck, P.J. et al, "Generation of Monoclonal Antibodies against Autologous Proteins in Gene-inactivated Mice," J. Biol. Chem., vol. 270(15) (1995) pp. 8397-8400.
Felgner, P.L. et al, "Lipofection: A Highly Efficient, Lipid-Mediated DNA-Transfection Procedure," Proc. Natl. Acad. Sci. USA, vol. 84(21) (1987) pp. 7413-7417.
Franz, G. et al, "Minos, a new transposable element from *Drosophila hydei*, is a member of the Tc1-like family of transposons," Nucl. Acids Res., vol. 19(23) (1991) p. 6646.
Hammer, R.E. et al, "Spontaneous Inflammatory Disease in Transgenic Rats Expressing HLA-B27 and Human $\beta_2$m: An Animal Model of HLA-B27-Associated Human Disorders," Cell, vol. 63 (1990) pp. 1099-1112.
Hickman, A.B. et al, "Molecular organization in site-specific recombination: The catalytic domain of bacteriophage HP1 integrase at 2.7 A resolution," Cell, vol. 89 (1997) pp. 227-237.
Houdebine, L.M. et al., "Transgenesis in fish," Experientia, vol. 47 (1991) pp. 891-897.
Hughes, B.J. et al., "Monoclonal Antibody Targeting of Liposomes to Mouse Lung in Vivo,"Cancer Research, vol. 49 (1989) pp. 6214-6220.
Ivics, Z. et al., "Identification of functional domains and evolution of Tc1-like transposable elements," Proc. Natl. Acad. Sci. USA, vol. 93(10) (1996) pp. 5008-5013.
Izsvak, Z. et al., "Characterization of a Tc1-like transposable element in zebrafish (*Danio rerio*)", Mol. Gen. Genet., vol. 247 (1995) pp. 312-322.
Izsvak, Z. et al., "Sleeping Beauty, a wide host-range transposon vector for genetic transformation in vertebrates," J. Mol. Biol., vol. 302 (2000) pp. 93-102.
Jakobovits, A., "Humanizing the mouse genome," Curr. Biol., vol. 4(8) (1994) pp. 761-763.
Joyner, A.L., et al., "Production of a mutation in mouse En-2 gene by homologous recombination in embryonic stem cells," Nature, vol. 338 (1989) pp. 153-156.
Ke, Z. et al, "Quetzal: a transposon of the Tc1 family in the mosquito Anolpheles albimanus" Genetica, vol. 98 (1996) pp. 141-147.
Kinsey, J.A., "Tad, a LINE-Like Transposable Element of Neurospora, Can Transpose Between Nuclei in Heterokaryons," Genetics, vol. 126 (Oct. 1990) pp. 317-323.
Kogan, G.L. et al., "The Gate retrotransposon in Drosophila melanogster: mobility in heterochromatin and aspects of its expression in germ line tissue," Mol. Genet Genomics, vol. 269(2) (2003) pp. 234-242.
Kuduvalli, P.N. et al, "Target DNA structure plays a critical role in Tn7 transposition." EMBO J. vol. 20(4) (2001) pp. 924-932.
Lakso, M. et al., "Targeted Oncogene Activation by Site-Specific Recombination in Transgenic Mice," PNAS, vol. 89(14) (1992) pp. 6232-6236.
Lam, W.L. et al., "Discovery of amphibian Tcl-like transposon families," J. Mol. Biol., vol. 257 (1996) pp. 359-366.
Lampe, D.J. et al, "Factors affecting transposition of the Himar1 Mariner transposon in vitro," Genetics, vol. 149(1) (1998) pp. 179-187.
Lee, S.S.T. et al., "Role of CYP2E1 in the Hepatotoxicity of Acetaminophen," J. Biol. Chem., vol. 271(20) (1996) pp. 1-16.
Li, Y. et al, "The P1 plasmid in action: time-lapse photomicroscopy reveals some unexpected aspects of plasmid partition," Plasmid, vol. 48(3) (2002) pp. 174-178.
Liang, H.C.L. et al., "Cypla2(−/−) null mutant mice develop normally but show deficient drug metabolism," PNAS, vol. 93 (Feb. 1996) pp. 1671-1676.
Lin, S. "Transgenic Zebrafish," Methods Mol. Bio., vol. 136 (2000) pp. 375-383.
Litzinger, D.C. et al., "Biodistribution and immunotargetability of ganglioside-stabilized dioleoylphosphatidylethanolamine liposomes," Biochimica et Biophysica Acta, vol. 1104 (1992) pp. 179-187.
Luan, D.D. et al., "Reverse Transcription of R2Bm RNA IS Primed by a Nick at the Chromosomal Target Site: A Mechanism for Non-LTR Retrotransposition," Cell, vol. 72 (1993) pp. 595-605.
Luan, D.D. et al, "RNA Template Requirements for Target DNA-Primed Reverse Transcription by the R2 Retrotransposable Element," Mol. Cell Biol., vol. 15(7) (1995) pp. 3882-3891.
Marra, D. et al., "Regulation of excision of the conjugative transposon," Mol. Microbiol, vol. 31(2) (1999) pp. 609-621.
Martin, C. et al., "CYP7B Generates a Selective Estrogen Receptor β Agonist in Human Prostrate," J. Clin. Endocr. Metab., vol. 89(6) (2004) pp. 2928-2935.
Merriman, P.J. et al., "S elements: a family of Tc1-like transposons in the genome of Drosolphila *melanogaster*," Genetics, vol. 141 (1995) pp. 1425-1438.
Nunes-Duby, S.E. et al, "Similarities and differences among 105 members of the Int family of site-specific recombinases," Nuc. Acids Res., vol. 26(2) (1998) pp. 391-406.
O'Gorman, S. et al., "Recombinase-Mediated Gene Activation and Site-Specific Integration in Mammalian Cells," Science, vol. 251(1991) pp. 1351-1355.

(56) References Cited

OTHER PUBLICATIONS

Pietersz, G.A. et al., "Antibody Conjugates for the Treatment of Cancer," Immunolog. Reviews, vol. 129 (1992) pp. 57-80.
Pursel, V.G. et al., "Genetic Engineering of Livestock," Science, vol. 244(4910) (1989) pp. 1281-1288.
Rezende, L.F. et al., "Essential Amino Acid Residues in the Single-stranded DNA-binding Protein of Bacteriophage T7, Identification of the Dimer Interface," J. Biol. Chem., vol. 277(52) (2002) pp. 50643-50653.
Roffler, S. et al., "Anti-neoplastic glucuronide prodrug treatment of human tumor cells targeted with a monoclonal antibody-enzyme conjugate," Biochem. Pharmacol., vol. 42(10) (1991) pp. 2062-2065.
Rose, K. et al., "Neurosteroid Hydroxylase CYP7B Vivid Reporter Activity in Dentate Gyrus of Gene-Targeted Mice and Abolition of a Widespread Pathway of Steroid and Oxysterol Hydroxylation," J. Biol. Chemistry, vol. 276 (2005) pp. 1-17.
Rubin, G.M. et al., "Genetic Transformation of *Drosophila* with Transposable Element Vectors," Science, vol. 218(4570) (1982) pp. 348-353.
Rubin, G.M. et al., "Vectors for P element mediated gene transfer in *Drosophila*," Nucleic Acids Res., vol. 11(18) (1983) pp. 6341-6351.
Senter, P.D. et al, "Generation of 5-Fluorouracil from 5-Fluorocytosine by Monoclonal Antibody-Cytosine Deaminase Conjugates," Bioconjugate Chem., vol. 2 (1991) pp. 447-451.
Senter, P.D. et al., "Generation of Cytotoxic Agents by Targeted Enzymes," Bioconjugate Chem., vol. 4 (1993) pp. 3-9.
Setchell, K.D.R. et al., "Identification of a New Inborn Error in Bile Acid Synthesis: Mutation of the Oxysterol 7α-Hydroxylase Gene Causes Severe Neonatal Liver Disease," J. Clin. Invest., vol. 102(9) (1998) pp. 1690-1703.
Shoemaker, N. B. et al., "The Bacteroides mobilizable insertion element, NBU1, integrates into the 3' end of a Leu-tRNA gene and has an integrase that is a member of the lambda integrase family," J. Bacteriol., vol. 178(12) (1996) pp. 3594-3600.
Sun, X. et al, "Conditional inactivation of Fgf4 reveals complexity of signaling during limb bud development," Nat. Genet. vol. 25 (2000) pp. 83-86.
The Gene Ontology Consortium, "Gene Ontology: tool for the unification of biology," Nature Genetics, vol. 25 (May 2000) pp. 25-29.
Toshiki, T. et al., "Germline transformation of the silkworm *Bombyx mori* L. using a piggyback transposon-derived vector," Nat. Biotechnol., vol. 18 (1) (Jan. 2000) pp. 81-84.
Tu, Z. et al., "Intra- and inter-specific diversity of Tc-3 like transposons in nematodes and insects and implications for their evolution and transposition," Gene, vol. 282 (2002) pp. 133-142.
Van Herwaarden, A.E. et al., "Knockout of cytochrome P450 3A yields new mouse models for understanding xenobiotic metabolism," J. Clin. Invest., vol. 117(11) (2007) p. 3583-3592.
Wilmut, I. et al, "Viable offspring derived from fetal and adult mammalian cells," Nature, vol. 385 (1997) pp. 810-813.
Wolff, J.A. et al, "Direct Gene Transfer into Mouse Muscle in Vivo," Science, vol. 247(1990) pp. 1465-1468.
Zhang, L. et al., "DNA-binding activity and subunit interaction of the marine transposase," Nucleic Acids Res., vol. 29(17) (2001) pp. 3566-3575.
Aitman, T. J., et al, Progress and prospects in rat genetics: a community view, Nature Genetics, May 2008, pp. 516-522, vol. 40, No. 5.
Geurts, A.M., et al, Generation of gene-specific mutated rats using zinc-finger nucleases, Rat Genomics: Methods of Molecular Biology, 2010, pp. 211-225, vol. 597 (Abstract only).
Jacob, H.J., et al, Gene Targeting in the Rat: Advances and Opportunities, Trends Genet., Dec. 2010, pp. 510-518, vol. 26(12).
Jacob, H.J., et al, Rat genetics: attaching physiology and pharmacology to the genome, Nature Reviews|Genetics, Jan. 2002, pp. 33-42, vol. 3.
Lu, B., Generation of rat mutants using a coat color-tagged Sleeping Beauty transposon system, Mamm Genome, 2007, pp. 338-346, vol. 18.
Mashimo, T, et al., Generation of knockout rats with X-linked severe combined immunodeficiency (X-SCID) using zinc-finger nucleases, PLoS One, Jan. 2010, pp. e8870 (1-7), vol. 5, Issue 1.
Tong, C. et al, Production of p53 gene knockout rats by homologous recombination in embryonic stem cells, Nature, Sep. 2010, pp. 211-213, vol. 467.

* cited by examiner

FIG. 3

Sequences encoding the transposases for the DNA transposons Sleeping Beauty and piggyBac:

SB Transposase:
ATGGGAAAATCAAAAGAAATCAGCCAAGACCTCAGAAAAAAAATTGTAGACCTCCACAAGTCTGGTTCATCCTTGGGAGCAATTT
CCAAACGCCTGAAAGTACCACGTTCATCTGTACAAACAATAGTACGCAAGTATAAACACCATGGGACCACGCAGCCGTCATACCG
CTCAGGAAGGAGACGCGTTCTGTCTCCTAGAGATGAACGTACTTTGGTGCGAAAAGTGCAAATCAATCCCAGAACAACAGCAAA
GGACCTTGTGAAGATGCTGGAGGAAACAGGTACAAAAGTATCTATATCCACAGTAAAACGAGTCCTATATCGACATAACCTGAAA
GGCCGCTCAGCAAGGAAGAAGCCACTGCTCCAAAACCGACATAAGAAAGCCAGACTACGGTTTGCAACTGCACATGGGGACAAA
GATCGTACTTTTTGGAGAAATGTCCTCTGGTCTGATGAAACAAAAATAGAACTGTTTGGCCATAATGACCATCGTTATGTTTGGAG
GAAGAAGGGGGAGGCTTGCAAGCCGAAGAACACCATCCCAACCGTGAAGCACGGGGGTGGCAGCATCATGTTGTGGGGGTGCTT
TGCTGCAGGAGGGACTGGTGCACTTCACAAAATAGATGGCATCATGAGGAAGGAAAATTATGTGGATATATTGAAGCAACATCTC
AAGACATCAGTCAGGAAGTTAAAGCTTGGTCGCAAATGGGTCTTCCAAATGGACAATGACCCCAAGCATACTTCCAAAGTTGTGG
CAAAATGGCTTAAGGACAACAAAGTCAAGGTATTGGAGTGGCCATCACAAAGCCCTGACCTCAATCCTATAGAAAATTTGTGGGC
AGAACTGAAAAAGCGTGTGCGAGCAAGGAGGCCTACAAACCTGACTCAGTTACACCAGCTCTGTCAGGAGGAATGGGCCAAAAT
TCACCCAACTTATTGTGGGAAGCTTGTGGAAGGCTACCCGAAACGTTTGACCCAAGTTAAACAATTTAAAGGCAATGCTACCAAA
TACTAG SB 5' ITR:
CAGTTGAAGTCGGAAGTTTACATACACTTAAGTTGGAGTCATTAAAACTCGTTTTTCAACTACTCCACAAATTTCTTGTTAACAAA
CAATAGTTTTGGCAAGTCAGTTAGGACATCTACTTTGTGCATGACACAAGTCATTTTTCCAACAATTGTTTACAGACAGATTATTTC
ACTTATAATTCACTGTATCACAATTCCAGTGGGTCAGAAGTTTACATACACTAAGT SB 3' ITR:
ATTGAGTGTATGTAAACTTCTGACCCACTGGGAATGTGATGAAAGAAATAAAAGCTGAAATGAATCATTCTCTCTACTATTATTCT
GATATTTCACATTCTTAAAATAAAGTGGTGATCCTAACTGACCTAAGACAGGGAATTTTTACTAGGATTAAATGTCAGGAATTGTG
AAAAAGTGAGTTTAAATGTATTTGGCTAAGGTGTATGTAAACTTCCGACTTCAACTG PB Transposase:
ATGGGTAGTTCTTTAGACGATGAGCATATCCTCTCTGCTCTTCTGCAAAGCGATGACGAGCTTGTTGGTGAGGATTCTGACAGTGA
AATATCAGATCACGTAAGTGAAGATGACGTCCAGAGCGATACAGAAGAAGCGTTTATAGATGAGGTACATGAAGTGCAGCCAAC
GTCAAGCGGTAGTGAAATATTAGACGAACAAAATGTTATTGAACAACCAGGTTCTTCATTGGCTTCTAACAGAATCTTGACCTTGC
CACAGAGGACTATTAGAGGTAAGAATAAACATTGTTGGTCAACTTCAAAGTCCACGAGGCGTAGCCGAGTCTCTGCACTGAACAT
TGTCAGATCTCAAAGAGGTCCGACGCGTATGTGCCGCAATATATATGACCCACTTTTATGCTTCAAACTATTTTTACTGATGAGA
TAATTTCGGAAATTGTAAAATGGACAAATGCTGAGATATCATTGAAACGTCGGGAATCTATGACAGGTGCTACATTTCGTGACAC
GAATGAAGATGAAATCTATGCTTTCTTTGGTATTCTGGTAATGACAGCAGTGAGAAAAGATAACCACATGTCCACAGATGACCTC
TTTGATCGATCTTTGTCAATGGTGTACGTCTCTGTAATGAGTCGTGATCGTTTTGATTTTTTGATACGATGTCTTAGAATGGATGAC
AAAAGTATACGGCCCACACTTCGAGAAAACGATGTATTTACTCCTGTTAGAAAAATATGGGATCTCTTTATCCATCAGTGCATACA
AAATTACACTCCAGGGGCTCATTTGACCATAGATGAACAGTTACTTGGTTTAGAGGACGGTGTCCGTTTAGGATGTATATCCCAA
ACAAGCCAAGTAAGTATGGAATAAAAATCCTCATGATGTGTGACAGTGGTACGAAGTATATGATAAATGGAATGCCTTATTTGGG
AAGAGGAACACAGACCAACGGAGTACCACTCGGTGAATACTACGTGAAGGAGTTATCAAAGCCTGTGCACGGTAGTTGTCGTAA
TATTACGTGTGACAATTGGTTCACCTCAATCCCTTTGGCAAAAAACTTACTACAAGAACCGTATAAGTTAACCATTGTGGGAACCG
TGCGATCAAACAAACGCGAGATACCGGAAGTACTGAAAAACAGTCGCTCCAGGCCAGTGGGAACATCGATGTTTTGTTTTGACGG
ACCCCTTACTCTCGTCTCATATAAACCGAAGCCAGCTAAGATGGTATACTTATTATCATCTTGTGATGAGGATGCTTCTATCAACG
AAAGTACCGGTAAACCGCAAATGGTTATGTATTATAATCAAACTAAAGGCGGAGTGGACACGCTAGACCAAATGTGTTCTGTGAT
GACCTGCAGTAGGAAGACGAATAGGTGGCCTATGGCATTATTGTACGGAATGATAAACATTGCCTGCATAAATTCTTTTATTATAT
ACAGCCATAATGTCAGTAGCAAGGGAGAAAAGGTTCAAAGTCGCAAAAAATTTATGAGAAACCTTTACATGAGCCTGACGTCATC
GTTTATGCGTAAGCGTTTAGAAGCTCCTACTTTGAAGAGATATTTGCGCGATAATATCTCTAATATTTTGCCAAATGAAGTGCCTG
GTACATCAGATGACAGTACTGAAGAGCCAGTAATGAAAAAACGTACTTACTGTACTTACTGCCCCTCTAAAATAAGGCGAAAGGC
AAATGCATCGTGCAAAAAATGCAAAAAAGTTATTTGTCGAGAGCATAATATTGATATGTGCCAAAGTTGTTTCTGA PB 5' ITR:
CCCTAGAAAGATAGTCTGCGTAAAATTGACGCATGCATTCTTGAAATATTGCTCTCTCTTTCTAAATAGCGCGAATCCGTCGCT
GTGCATTTAGGACATCTCAGTCGCCGCTTGGAGCTCCCGTGAGGCGTGCTTGTCAATGCGGTAAGTGTCACTGATTTTGAACTATA
ACGACCGCGTGAGTCAAAATGACGCATGATTATCTTTTACGTGACTTTTAAGATTTAACTCATACGATAATTATATTGTTATTTCAT
GTTCTACTTACGTGATAACTTATTATATATATATTTTCTTGTTATAGATATC (minimal sequence is underlined and bold, i.e., first 35 bp)

PB 3' ITR:
TAAAAGTTTTGTTACTTTATAGAAGAAATTTTGAGTTTTTGTTTTTTTTTAATAAATAAATAAACATAAATAAATTGTTTGTTGAAT
TTATTATTAGTATGTAAGTGTAAATATAATAAAACTTAATATCTATTCAAATTAATAAATAAACCTCGATATACAGACCGATAAAA
CACATGCGTCAATTTTACGCATGATTATCTTTAACGTACGTCACAATATGATTATCTTTCTAGGG (minimal sequence is underlined and bold, i.e., first 35 bp)

FIG. 4
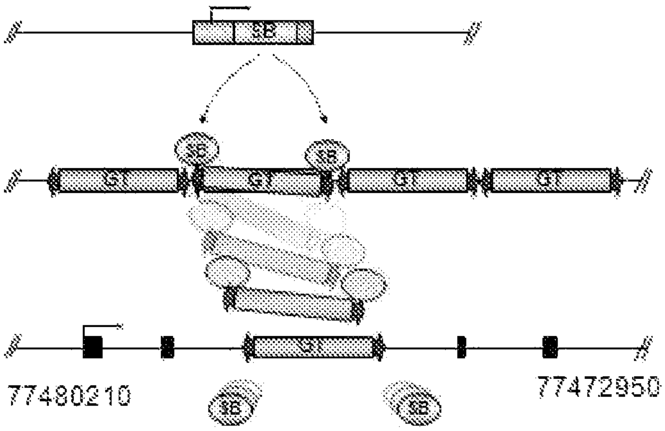
Figure 4 Legend
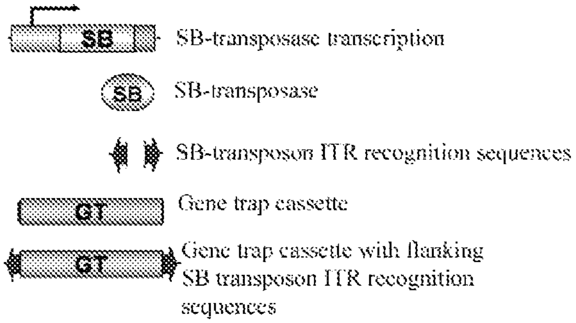

GENETICALLY MODIFIED RAT COMPRISING A CYTOKINE GENE DISRUPTION AND EXHIBITING A GREATER SUSCEPTIBILITY TO A CYTOKINE-MEDIATED AUTOIMMUNE AND/OR INFLAMMATORY DISEASE

CROSS-REFERENCE TO RELATED APPLICATIONS

This application claims the benefit of U.S. Provisional Patent Application Ser. No. 61/228,369, filed Jul. 24, 2009, which application is hereby incorporated by reference in its entirety for all purposes.

BACKGROUND OF THE INVENTION

Gene modification is a process whereby a specific gene, or a fragment of that gene, is altered. This alteration of the targeted gene may result in a change in the level of RNA and/or protein that is encoded by that gene, or the alteration may result in the targeted gene encoding a different RNA or protein than the untargeted gene. The modified gene may be studied in the context of a cell, or, more preferably, in the context of a genetically modified animal.

Genetically modified animals are among the most useful research tools in the biological sciences. An example of a genetically modified animal is a transgenic animal, which has a heterologous (i.e., foreign) gene, or gene fragment, incorporated into their genome that is passed on to their offspring. Although there are several methods of producing genetically modified animals, the most widely used is microinjection of DNA into single cell embryos. These embryos are then transferred into pseudopregnant recipient foster mothers. The offspring are then screened for the presence of the new gene, or gene fragment. Potential applications for genetically modified animals include discovering the genetic basis of human and animal diseases, generating disease resistance in humans and animals, gene therapy, toxicology studies, drug testing, and production of improved agricultural livestock.

Identification of novel genes and characterization of their function using mutagenesis has also been shown to be productive in identifying new drugs and drug targets. Creating in vitro cellular models that exhibit phenotypes that are clinically relevant provides a valuable substrate for drug target identification and screening for compounds that modulate not only the phenotype but also the target(s) that controls the phenotype. Modulation of such a target can provide information that validates the target as important for therapeutic intervention in a clinical disorder when such modulation of the target serves to modulate a clinically relevant phenotype.

Cytokines are effective regulatory elements which are secreted by the immune system upon activation. The cytokine-cytokine signaling pathway controls immune responses such as B-, T-, and NK-cell activation and proliferation. The cytokine-cytokine signaling pathway enables production of macrophages and immunoglobulins upon activation. In order to control levels of lymphocytes the cytokine-cytokine signaling pathway also facilitates programmed cell death or apoptosis when auxiliary cells exist. The pathway controls antibody response to antigens and pathogens. Since this pathway is a very important regulator of immune response, alterations can cause profound dysregulation which leads to disease states in both animal models and humans.

Animal models with an alteration in the cytokine-cytokine signaling pathway are critical for studies of the basic mechanisms in autoimmunity. Altered cytokine-cytokine signaling models display autoimmune phenotypes such as spontaneous polyclonal B-cell activation (PBA), the production of high titers of autoantibodies to native DNA, and uncontrolled proliferation of lymphocytes. The dysregulation of immune responses displayed in these models resembles human chronic inflammatory diseases and autoimmune diseases such as Inflammatory Bowel Disease (IBD), Rheumatoid Arthritis (RA), and Systemic Lupus Erythematosus (SLE). The autoimmune cytokine-cytokine signaling defective rat presents an important advantage over mouse models for autoimmune diseases. The rat provides up to ten times for sera sample which is critical for accurate measure of lymphocyte production. The rat is also larger providing a means by which investigators can perform instrumentation studies such as colon scopes, or imaging studies, which are impossible in mouse models. Rat models of cytokine-cytokine mediated autoimmune disease provide a more effective method for studying the molecular basis of autoimmune disease and development of therapeutic intervention to alleviate such diseases.

Animal models exhibiting clinically relevant phenotypes are also valuable for drug discovery and development and for drug target identification. For example, mutation of somatic or germ cells facilitates the production of genetically modified offspring or cloned animals having a phenotype of interest. Such animals have a number of uses, for example as models of physiological disorders (e.g., of human genetic diseases) that are useful for screening the efficacy of candidate therapeutic compounds or compositions for treating or preventing such physiological disorders. Furthermore, identifying the gene(s) responsible for the phenotype provides potential drug targets for modulating the phenotype and, when the phenotype is clinically relevant, for therapeutic intervention. In addition, the manipulation of the genetic makeup of organisms and the identification of new genes have important uses in agriculture, for example in the development of new strains of animals and plants having higher nutritional value or increased resistance to environmental stresses (such as heat, drought, or pests) relative to their wild-type or non-mutant counterparts.

Since most eukaryotic cells are diploid, two copies of most genes are present in each cell. As a consequence, mutating both alleles to create a homozygous mutant animal is often required to produce a desired phenotype, since mutating one copy of a gene may not produce a sufficient change in the level of gene expression or activity of the gene product from that in the non-mutated or wild-type cell or multicellular organism, and since the remaining wild-type copy would still be expressed to produce functional gene product at sufficient levels. Thus, to create a desired change in the level of gene expression and/or function in a cell or multicellular organism, at least two mutations, one in each copy of the gene, are often required in the same cell.

In other instances, mutation in multiple different genes may be required to produce a desired phenotype. In some instances, a mutation in both copies of a single gene will not be sufficient to create the desired physiological effects on the cell or multi-cellular organism. However, a mutation in a second gene, even in only one copy of that second gene, can reduce gene expression levels of the second gene to produce a cumulative phenotypic effect in combination with the first mutation, especially if the second gene is in the same general biological pathway as the first gene. This effect can alter the function of a cell or multi-cellular organism. A hypomorphic mutation in either gene alone could result in protein levels that are severely reduced but with no overt effect on physiology. Severe reductions in the level of expression of both genes, however, can have a major impact. This principle can be extended to other instances where mutations in multiple (two, three, four, or more, for example) genes are required cumulatively to produce an effect on activity of a gene product or on another phenotype in a cell or multi-cellular organism. It should be noted that, in this instance, such genes may all be expressed in the same cell type and therefore, all of the required mutations occur in the same cell. However, the genes may normally be expressed in different cell types (for example, secreting the different gene products from the different cells). In this case, the gene products are expressed in different cells but still have a biochemical relationship such that one or more mutations in each gene is required to produce the desired phenotype.

BRIEF SUMMARY OF THE INVENTION

In accordance with the purposes of this invention, as embodied and broadly described herein, this invention relates to the engineering of animal cells, preferably mammalian, more preferably rat, that are deficient due to the disruption of gene(s) or gene product(s) resulting in cytokine-cytokine mediated autoimmune and inflammatory disease.

In another aspect, the invention relates to genetically modified rats, as well as the descendants and ancestors of such animals, which are animal models of human autoimmune and inflammatory disease and methods of their use.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWING

This invention, as defined in the claims, can be better understood with reference to the following drawings:

FIGS. 1-4 show the process for creating a genetically modified cytokine-cytokine mediated autoimmune and inflammatory disease rat model using DNA transposons to create an insertion mutation directly in the germ line.

FIG. 1: Gene modification by DNA transposons.

FIG. 2: Breeding strategy for creating rat knockouts directly in the germ cells with DNA transposons.

FIG. 3: DNA sequences

FIG. 4: DNA transposon-mediated insertion mutation in *Rattus norvegicus* Faslg gene.

Figure 1:
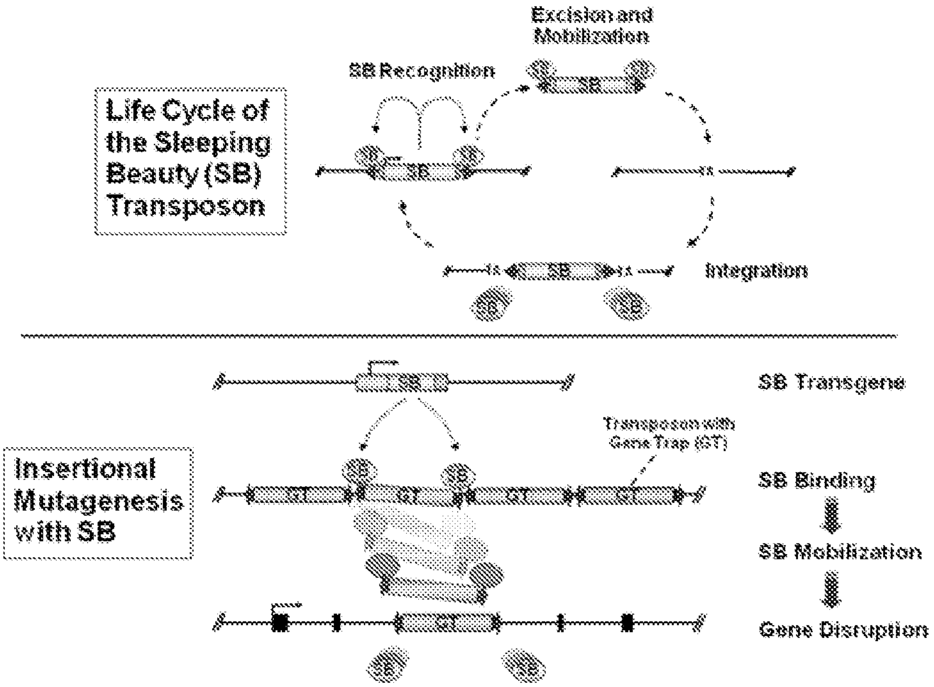

In the following description of the illustrated embodiments, references are made to the accompanying drawings, which form a part hereof, and in which is shown by way of illustration various embodiments in which the invention may be practiced. It is to be understood that other embodiments may be utilized and structural and functional changes may be made without departing from the scope of the present invention.

DETAILED DESCRIPTION OF THE INVENTION

Definitions

The present invention may be understood more readily by reference to the following detailed description of preferred embodiments of the invention and the Examples included therein and to the Figures and their previous and following description. Although any methods and materials similar or equivalent to those described herein can be used in the practice or testing of the present invention, the preferred methods, devices, and materials are now described. All references, publications, patents, patent applications, and commercial materials mentioned herein are incorporated herein by reference for the purpose of describing and disclosing the materials and/or methodologies which are reported in the publications which might be used in connection with the invention. Nothing herein is to be construed as an admission that the invention is not entitled to antedate such disclosure by virtue of prior invention.

Before the present compounds, compositions, articles, devices, and/or methods are disclosed and described, it is to be understood that this invention is not limited to specific synthetic methods, specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

Throughout this application, reference is made to various proteins and nucleic acids. It is understood that any names used for proteins or nucleic acids are art-recognized names, such that the reference to the name constitutes a disclosure of the molecule itself.

As used in the specification and the appended claims, the singular forms “a,” “an” and “the” include plural referents unless the context clearly dictates otherwise. Thus, for example, reference to “a pharmaceutical carrier” includes mixtures of two or more such carriers, and the like.

Ranges may be expressed herein as from “about” one particular value, and/or to “about” another particular value. When such a range is expressed, another embodiment includes from the one particular value and/or to the other particular value. Similarly, when values are expressed as approximations, by use of the antecedent “about,” it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings:

A “coding sequence” or a sequence “encoding” an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

“Complementary,” as used herein, refers to the subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs).

A “deletion mutation” means a type of mutation that involves the loss of genetic material, which may be from a single base to an entire piece of chromosome. Deletion of one or more nucleotides in the DNA could alter the reading frame of the gene; hence, it could result in a synthesis of a nonfunctional protein due to the incorrect sequence of amino acids during translation.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed". An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "gene", also called a "structural gene" means a DNA sequence that codes for or corresponds to a particular sequence of amino acids which comprise all or part of one or more proteins or enzymes, and may or may not include introns and regulatory DNA sequences, such as promoter sequences, 5'-untranslated region, or 3'-untranslated region which affect for example the conditions under which the gene is expressed. Some genes, which are not structural genes, may be transcribed from DNA to RNA, but are not translated into an amino acid sequence. Other genes may function as regulators of structural genes or as regulators of DNA transcription.

By "genetically modified" is meant a gene that is altered from its native state (e.g. by insertion mutation, deletion mutation, nucleic acid sequence mutation, or other mutation), or that a gene product is altered from its natural state (e.g. by delivery of a transgene that works in trans on a gene's encoded mRNA or protein, such as delivery of inhibitory RNA or delivery of a dominant negative transgene).

By "exon" is meant a region of a gene which includes sequences which are used to encode the amino acid sequence of the gene product.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is such an element operatively associated with a different gene than the one it is operatively associated with in nature.

As used herein, the term "homology" refers to the subunit sequence identity or similarity between two polymeric molecules e.g., between two nucleic acid molecules, e.g., between two DNA molecules, or two polypeptide molecules. When a subunit position in both of the two molecules is occupied by the same monomeric subunit, e.g., if a position in each of two polypeptide molecules is occupied by phenylalanine, then they are identical at that position. The homology between two sequences, most clearly defined as the % identity, is a direct function of the number of identical positions, e.g., if half (e.g., 5 positions in a polymer 10 subunits in length) of the positions in two polypeptide sequences are identical then the two sequences are 50% identical; if 70% of the positions, e.g., 7 out of 10, are matched or homologous, the two sequences share 70% identity. By way of example, the polypeptide sequences ACDEFG and ACDHIK share 50% identity and the nucleotide sequences CAATCG and CAAGAC share 50% identity.

"Homologous recombination" is the physical exchange of DNA expedited by the breakage and reunion of two non-sister chromatids. In order to undergo recombination the DNA duplexes must have complementarity. The molecular mechanism is as follows: DNA duplexes pair, homologous strands are nicked, and broken strands exchange DNA between duplexes. The region at the site of recombination is called the hybrid DNA or heteroduplex DNA. Second nicks are made in the other strand, and the second strand crosses over between duplexes. After this second crossover event the reciprocal recombinant or splice recombinant is created. The duplex of one DNA parent is covalently linked to the duplex of another DNA parent. Homologous recombination creates a stretch of heteroduplex DNA.

A "hypomorphic mutation" is a change to the genetic material (usually DNA or RNA), which can be caused by any form of genetic mutation, and causes an decrease in normal gene function without causing a complete absence of normal gene function.

The term "inbred animal" is used herein to refer to an animal that has been interbred with other similar animals of the same species in order to preserve and fix certain characteristics, or to prevent other characteristics from being introduced into the breeding population.

The term "insertional mutation" is used herein to refer the translocation of nucleic acid from one location to another location which is in the genome of an animal so that it is integrated into the genome, thereby creating a mutation in the genome. Insertional mutations can also include knocking out or knocking in of endogenous or exogenous DNA via gene trap or cassette insertion. Exogenous DNA can access the cell via electroporation or chemical transformation. If the exogenous DNA has homology with chromosomal DNA it will align itself with endogenous DNA. The exogenous DNA is then inserted or disrupts the endogenous DNA via two adjacent crossing over events, known as homologous recombination. A targeting vector can use homologous recombination for insertional mutagenesis. Insertional mutagenesis of endogenous or exogenous DNA can also be carried out via DNA transposon. The DNA transposon is a mobile element that can insert itself along with additional exogenous DNA into the genome. Insertional mutagenesis of endogenous or exogenous DNA can be carried out by retroviruses. Retroviruses have a RNA viral genome that is converted into DNA by reverse transcriptase in the cytoplasm of the infected cell. Linear retroviral DNA is transported into the nucleus, and become integrated by an enzyme called integrase. Insertional mutagenesis of endogenous or exogenous DNA can also be done by retrotransposons in which an RNA intermediate is translated into DNA by reverse transcriptase, and then inserted into the genome.

The term "gene knockdown" refers to techniques by which the expression of one or more genes is reduced, either through genetic modification (a change in the DNA of one of the organism's chromosomes) or by treatment with a reagent such as a short DNA or RNA oligonucleotide with a sequence complementary to either an mRNA transcript or a gene. If genetic modification of DNA is done, the result is a "knockdown organism" or "knockdowns".

By "knock-out" is meant an alteration in the nucleic acid sequence that reduces the biological activity of the polypeptide normally encoded therefrom by at least 80% compared to the unaltered gene. The alteration may be an insertion, deletion, frameshift mutation, or missense mutation. Preferably, the alteration is an insertion or deletion, or is a frameshift mutation that creates a stop codon.

An "L1 sequence" or "L1 insertion sequence" as used herein, refers to a sequence of DNA comprising an L1 element comprising a 5' UTR, ORF1 and ORF2, a 3' UTR and a poly A signal, wherein the 3' UTR has DNA (e.g. a gene trap or other cassette) positioned either therein or positioned between the 3' UTR and the poly A signal, which DNA is to be inserted into the genome of a cell.

A "mutation" is a detectable change in the genetic material in the animal, which is transmitted to the animal's progeny. A mutation is usually a change in one or more deoxyribonucleotides, the modification being obtained by, for example, adding, deleting, inverting, or substituting nucleotides. Exemplary mutations include but are not limited to a deletion mutation, an insertion mutation, a non-sense mutation or a missense mutation. Thus, the terms "mutation" or "mutated" as used herein are intended to denote an alteration in the "normal" or "wild-type" nucleotide sequence of any nucleotide sequence or region of the allele. As used herein, the terms "normal" and "wild-type" are intended to be synonymous, and to denote any nucleotide sequence typically found in nature. The terms "mutated" and "normal" are thus defined relative to one another; where a cell has two chromosomal alleles of a gene that differ in nucleotide sequence, at least one of these alleles is a "mutant" allele as that term is used herein. Based on these definitions, an "endogenous cytokine gene" is the "wild-type" gene that exists normally in a cell, and a "mutated cytokine gene" defines a gene that differs in nucleotide sequence from the wild-type gene.

"Non-homologous end joining (NHEJ)" is a cellular repair mechanism. The NHEJ pathway is defined by the ligation of blunt ended double stand DNA breaks. The pathway is initiated by double strand breaks in the DNA, and works through the ligation of DNA duplex blunt ends. The first step is recognition of double strand breaks and formation of scaffold. The trimming, filling in of single stranded overhangs to create blunt ends and joining is executed by the NHEJ pathway. An example of NHEJ is repair of a DNA cleavage site created by a zinc finger nuclease (ZFN). This would normally be expected to create a small deletion mutation.

"Nucleic Acid sequence mutation" is a mutation to the DNA of a gene that involves change of one or multiple nucleotides. A point mutation which affects a single nucleotide can result in a transition (purine to purine or pyrimidine to pyrimidine) or a transversion (purine to pyrimidine or pyrimidine to purine). A point mutation that changes a codon to represent a different amino acid is a missense mutation. Some point mutations can cause a change in amino acid so that there is a premature stop codon; these mutations are called nonsense mutations. A mutation that inserts or deletes a single base will change the entire downstream sequence and are known as frameshift mutations. Some mutations change a base pair but have no effect on amino acid representation; these are called silent mutations. Mutations to the nucleic acid of a gene can have different consequences based on their location (intron, exon, regulatory sequence, and splice joint).

"Optional" or "optionally" means that the subsequently described event or circumstance may or may not occur, and that the description includes instances where said event or circumstance occurs and instances where it does not.

The term "outbred animal" is used herein to refer to an animal that breeds with any other animal of the same species without regard to the preservation of certain characteristics.

As used herein, the term "phenotype" means any property of a cell or organism. A phenotype can simply be a change in expression of an mRNA or protein. Examples of phenotypes also include, but are in no way limited to, cellular, biochemical, histological, behavioral, or whole organismal properties that can be detected by the artisan. Phenotypes include, but are not limited to, cellular transformation, cell migration, cell morphology, cell activation, resistance or sensitivity to drugs or chemicals, resistance or sensitivity to pathogenic protein localization within the cell (e.g. translocation of a protein from the cytoplasm to the nucleus), resistance or sensitivity to ionizing radiation, profile of secreted or cell surface proteins, (e.g., bacterial or viral) infection, post-translational modifications, protein localization within the cell (e.g. translocation of a protein from the cytoplasm to the nucleus), profile of secreted or cell surface proteins, cell proliferation, signal transduction, metabolic defects or enhancements, transcriptional activity, recombination intermediate joining, DNA damage response, cell or organ transcript profiles (e.g., as detected using gene chips), apoptosis resistance or sensitivity, animal behavior, organ histology, blood chemistry, biochemical activities, gross morphological properties, life span, tumor susceptibility, weight, height/length, immune function, organ function, any disease state, and other properties known in the art. In certain situations and therefore in certain embodiments of the invention, the effects of mutation of one or more genes in a cell or organism can be determined by observing a change in one or more given phenotypes (e.g., in one or more given structural or functional features such as one or more of the phenotypes indicated above) of the mutated cell or organism compared to the same structural or functional feature(s) in a corresponding wild-type or (non-mutated) cell or organism (e.g., a cell or organism in which the gene(s) have not been mutated).

By "plasmid" is meant a circular strand of nucleic acid capable of autosomal replication in plasmid-carrying bacteria. The term includes nucleic acid which may be either DNA or RNA and may be single- or double-stranded. The plasmid of the definition may also include the sequences which correspond to a bacterial origin of replication.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. The promoter may be operatively associated with other expression control sequences, including enhancer and repressor sequences.

A "random site" is used herein to refer to a location in the genome where a retrotransposition or transposition or other DNA mutation event takes places, without prior intention of mutation at that particular location. It is also used herein to refer to a location in the genome that is randomly modified by any insertion mutation or deletion mutation or nucleic acid sequence mutation.

The term "regulatory sequence" is defined herein as including promoters, enhancers and other expression control elements such as polyadenylation sequences, matrix attachment sites, insulator regions for expression of multiple genes on a single construct, ribosome entry/attachment sites, introns that are able to enhance expression, and silencers.

By "reporter gene" is meant any gene which encodes a product whose expression is detectable. A reporter gene product may have one of the following attributes, without restriction: fluorescence (e.g., green fluorescent protein), enzymatic activity (e.g., lacZ or luciferase), or an ability to be specifically bound by a second molecule (e.g., biotin or an antibody-recognizable epitope).

By "retrotransposition" as used herein, is meant the process of integration of a sequence into a genome, expression of that sequence in the genome, reverse transcription of the integrated sequence to generate an extrachromosomal copy of the sequence and reintegration of the sequence into the genome.

A "retrotransposition event" is used herein to refer to the translocation of a retrotransposon from a first location to a second location with the preferable outcome being integration of a retrotransposon into the genome at the second location. The process involves a RNA intermediate, and can retrotranspose from one chromosomal location to another or from introduced exogenous DNA to endogenous chromosomal DNA.

By "selectable marker" is meant a gene product which may be selected for or against using chemical compounds, especially drugs. Selectable markers often are enzymes with an ability to metabolize the toxic drugs into non-lethal products. For example, the pac (puromycin acetyl transferase) gene product can metabolize puromycin, the dhfr gene product can metabolize trimethoprim (tmp) and the bla gene product can metabolize ampicillin (amp). Selectable markers may convert a benign drug into a toxin. For example, the HSV tk gene product can change its substrate, FIAU, into a lethal substance. Another selectable marker is one which may be utilized in both prokaryotic and eukaryotic cells. The neo gene, for example, metabolizes and neutralizes the toxic effects of the prokaryotic drug, kanamycin, as well as the eukaryotic drug, G418.

By "selectable marker gene" as used herein is meant a gene or other expression cassette which encodes a protein which facilitates identification of cells into which the selectable marker gene is inserted.

A "specific site" is used herein to refer to a location in the genome that is predetermined as the position where a retrotransposition or transposition event or other DNA mutation will take place. It is also used herein to refer to a specific location in the genome that is modified by any insertion mutation or deletion mutation or nucleic acid sequence mutation.

A "cytokine gene" is used herein to refer to a gene which encodes a protein that is associated with the phenotype that is characterized as cytokine-cytokine mediated autoimmune and inflammatory disease. This phenotype ranges from lymphocyte proliferation, macrophage and immunoglobulin dysfunction, native DNA autoantibody production, contact sensitivity deficiency, and chronic inflammation. A "cytokine protein" is used herein to refer to a protein product of a gene that is associated with the phenotype that is characterized as cytokine-cytokine mediated autoimmune and inflammatory disease.

As used herein, the term "targeted genetic recombination" refers to a process wherein recombination occurs within a DNA target locus present in a host cell or host organism. Recombination can involve either homologous or non-homologous DNA.

The term "transfection" means the introduction of a foreign nucleic acid into a cell. The term "transformation" means the introduction of a "foreign" (i.e. extrinsic or extracellular) gene, DNA or RNA sequence to an ES cell or pronucleus, so that the cell will express the introduced gene or sequence to produce a desired substance in a genetically modified animal.

By "transgenic" is meant any animal which includes a nucleic acid sequence which is inserted by artifice into a cell and becomes a part of the genome of the animal that develops from that cell. Such a transgene may be partly or entirely heterologous to the transgenic animal. Although transgenic mice represent another embodiment of the invention, other transgenic mammals including, without limitation, transgenic rodents (for example, hamsters, guinea pigs, rabbits, and rats), and transgenic pigs, cattle, sheep, and goats are included in the definition.

By "transposition" as used herein, is meant the process of one DNA sequence insertion into another (location) without relying on sequence homology. The DNA element can be transposed from one chromosomal location to another or from introduction of exogenous DNA and inserted into the genome.

A "transposition event" or "transposon insertion sequence" is used herein to refer to the translocation of a DNA transposon either from one location on the chromosomal DNA to another or from one location on introduced exogenous DNA to another on the chromosomal DNA.

By "transposon" or "transposable element" is meant a linear strand of DNA capable of integrating into a second strand of DNA which may be linear or may be a circularized plasmid. Transposons often have target site duplications, or remnants thereof, at their extremities, and are able to integrate into similar DNA sites selected at random, or nearly random. Preferred transposons have a short (e.g., less than 300) base pair repeat at either end of the linear DNA. By "transposable elements" is meant any genetic construct including but not limited to any gene, gene fragment, or nucleic acid that can be integrated into a target DNA sequence under control of an integrating enzyme, often called a transposase.

A coding sequence is "under the control of" or "operatively associated with" transcriptional and translational control sequences in a cell when RNA polymerase transcribes the coding sequence into mRNA, which is then trans-RNA spliced (if it contains introns) and translated, in the case of mRNA, into the protein encoded by the coding sequence.

The term "variant" may also be used to indicate a modified or altered gene, DNA sequence, enzyme, cell, etc., i.e., any kind of mutant.

The term "vector" is used interchangeably with the terms "construct", "cloning vector" and "expression vector" and means the vehicle by which a DNA or RNA sequence (e.g. a foreign gene) can be introduced into a host cell, (e.g. ES cell or pronucleus) so as to transform the host and promote expression (e.g. transcription and translation) of the introduced sequence including but not limited to plasmid, phage, transposons, retrotransposons, viral vector, and retroviral vector. By "non-viral vector" is meant any vector that does not comprise a virus or retrovirus.

A "vector sequence" as used herein, refers to a sequence of DNA comprising at least one origin of DNA replication and at least one selectable marker gene.

For the purposes of the present invention, the term "zinc finger nuclease" or "ZFN" refers to a chimeric protein molecule comprising at least one zinc finger DNA binding domain effectively linked to at least one nuclease or part of a nuclease capable of cleaving DNA when fully assembled. Ordinarily, cleavage by a ZFN at a target locus results in a double stranded break (DSB) at that locus.

The present invention provides a desired rat or a rat cell which contains a predefined, specific and desired alteration rendering the rat or rat cell predisposed to cytokine-cytokine mediated autoimmune and inflammatory disease. Specifically, the invention pertains to a genetically altered rat, or a rat cell in culture, that is defective in at least one of two alleles of a cytokine gene such as the Faslg gene, the Fas gene, etc. In one embodiment, the cytokine gene is the Faslg gene. In another embodiment, the cytokine gene is one of several known cytokine genes, such as Fas, IFNγ, TNF-α, IL-2, IL-10, and IL-12. The inactivation of at least one of these cytokine alleles results in an animal with a higher susceptibility to cytokine-cytokine mediated autoimmune and inflammatory disease induction. In one embodiment, the genetically altered animal is a rat of this type and is able to serve as a useful model for cytokine-cytokine mediated autoimmune and inflammatory disease and as a test animal for autoimmune and other studies. The invention additionally pertains to the use of such rats or rat cells, and their progeny in research and medicine.

In one embodiment, the invention provides a genetically modified or chimeric rat cell whose genome comprises two chromosomal alleles of a cytokine gene (especially, the Faslg gene), wherein at least one of the two alleles contains a mutation, or the progeny of this cell. The invention includes the embodiment of the above animal cell, wherein one of the alleles expresses a normal cytokine gene product. The invention includes the embodiment wherein the rat cell is a pluripotent cell such as an embryonic cell, embryonic stem (ES) cell, induced pluripotent stem cell (iPS), or spermatagonial stem (SS) cell, and in particular, wherein the cytokine gene is the gene. In another embodiment, the cytokine gene is one of several known cytokine genes, such as Fas, IFNγ, TNF-α, IL-2, IL-10, IL-12, Cxcr2(Il8rb), Ccr4, Ccr9, Cx3cr1, and Vegf. In another embodiment, the rat cell is a somatic cell.

The methods of the present invention can be used to mutate any eukaryotic cell, including, but not limited to, haploid (in the case of multiple gene mutations), diploid, triploid, tetraploid, or aneuploid. In one embodiment, the cell is diploid. Cells in which the methods of the present invention can be advantageously used include, but are not limited to, primary cells (e.g., cells that have been explanted directly from a donor organism) or secondary cells (e.g., primary cells that have been grown and that have divided for some period of time in vitro, e.g., for 10-100 generations). Such primary or secondary cells can be derived from multi-cellular organisms, or single-celled organisms. The cells used in accordance with the invention include normal cells, terminally differentiated cells, or immortalized cells (including cell lines, which can be normal, established or transformed), and can be differentiated (e.g., somatic cells or germ cells) or undifferentiated (e.g., multipotent, pluripotent or totipotent stem cells).

A variety of cells isolated from the above-referenced tissues, or obtained from other sources (e.g., commercial sources or cell banks), can be used in accordance with the invention. Non-limiting examples of such cells include somatic cells such as immune cells (T-cells, B-cells, Natural Killer (NK) cells), blood cells (erythrocytes and leukocytes), endothelial cells, epithelial cells, neuronal cells (from the central or peripheral nervous systems), muscle cells (including myocytes and myoblasts from skeletal, smooth or cardiac muscle), connective tissue cells (including fibroblasts, adipocytes, chondrocytes, chondroblasts, osteocytes and osteoblasts) and other stromal cells (e.g., macrophages, dendritic cells, thymic nurse cells, Schwann cells, etc.). Eukaryotic germ cells (spermatocytes and oocytes) can also be used in accordance with the invention, as can the progenitors, precursors and stem cells that give rise to the above-described somatic and germ cells. These cells, tissues and organs can be normal, or they can be pathological such as those involved in diseases or physical disorders, including but not limited to immune related diseases, chronic inflammation, autoimmune responses, infectious diseases (caused by bacteria, fungi or yeast, viruses (including HIV) or parasites), in genetic or biochemical pathologies (e.g., cystic fibrosis, hemophilia, Alzheimer's disease, schizophrenia, muscular dystrophy, multiple sclerosis, etc.), or in carcinogenesis and other cancer-related processes. Rat pluripotent cells, including embryonic cells, spermatogonial stem cells, embryonic stem cells, and iPS cells are envisioned. Rat somatic cells are also envisioned.

In certain embodiments of the invention, cells can be mutated within the organism or within the native environment as in tissue explants (e.g., in vivo or in situ). Alternatively, tissues or cells isolated from the organism using art-known methods and genes can be mutated according to the present methods. The tissues or cells are either maintained in culture (e.g., in vitro), or re-implanted into a tissue or organism (e.g., ex vivo).

The invention also includes a non-human genetically modified or chimeric rat whose genome comprises two chromosomal alleles of a cytokine gene, wherein at least one of the two alleles contains a mutation, or the progeny of the animal, or an ancestor of the animal, at an embryonic stage (preferably the one-cell, or fertilized oocyte stage, and generally, not later than about the 8-cell stage) contains a mutation. The invention also includes the embodiment wherein the cytokine gene of the rat is the Faslg gene. In another embodiment, the cytokine gene is one of several known cytokine genes, such as Fas, IFNγ, TNF-α, IL-2, IL-10, IL-12, Cxcr2(Il8rb), Ccr4, Ccr9, Cx3cr1, and Vegf. The invention is also directed to the embodiment wherein the animal cell is a rat pluripotent cell. The invention is also directed to the embodiment wherein the animal cell is a rat somatic cell.

Figure 2:
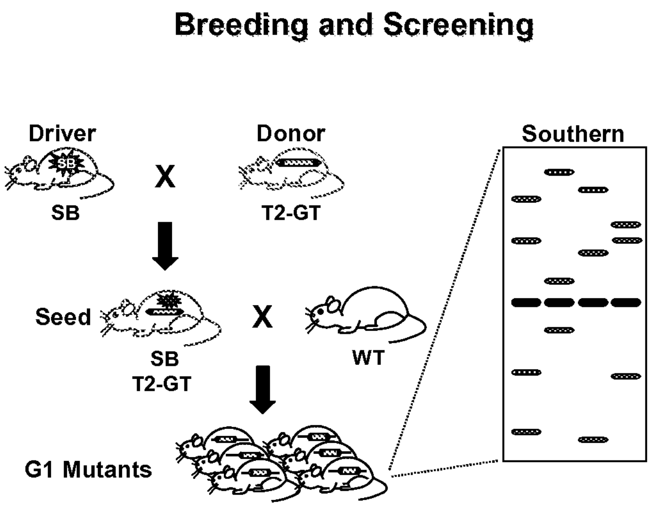

In one embodiment, the cytokine gene is mutated directly in the germ cells of a living organism. The separate transgenes for DNA transposon flanking ends and transposase are facilitated to create an active DNA transposon which integrates into the rat's genome. A plasmid containing transposon inverted repeats is used to create the transgenic "donor" rat. A plasmid containing transposase is used to create a separate transgenic "driver" rat. The donor rat is then bred with the driver rat to produce a rat which contains both donor transposon with flanking repeats and driver transposase (FIG. 2). This rat known as the "seed" rat has an activated DNA transposase which drives transposition events. The seed rat is bred to wild type rats to create heterozygote progeny with new transposon insertions. The heterozygotes can be interbred to create homozygous rats. Transposon insertion mutations are identified and recovered via a cloning and sequencing strategy involving the transposon-cellular DNA junction fragments. The rats that are identified to have a new DNA transposon insertion in a known gene or EST or DNA sequence of interest are called knockout rats.

In one embodiment, the cytokine gene is mutated in the oocyte before fusion of the pronuclei. This method for genetic modification of rats uses microinjected DNA into the male pronucleus before nuclear fusion. The microinjected DNA creates a genetically modified founder rat. A female rat is mated and the fertilized eggs are flushed from their oviducts. After entry of the sperm into the egg, the male and female pronuclei are separate entities until nuclear fusion occurs. The male pronucleus is larger are can be identified via dissecting microscope. The egg can be held in place by micromanipulation using a holding pipette. The male pronucleus is then microinjected with DNA that can be genetically modified. The microinjected eggs are then implanted into a surrogate pseudopregnant female which was mated with a vasectomized male for uterus preparation. The foster mother gives birth to genetically modified animal. The microinjection method can introduce genetic modifications directly to the germline of a living animal.

In another embodiment, the cytokine gene is mutated in a pluripotent cell. These pluripotent cells can proliferate in cell culture and be genetically modified without affecting their ability to differentiate into other cell types including germline cells. Genetically modified pluripotent cells from a donor can be microinjected into a recipient blastocyst, or in the case of spermatogonial stem cells can be injected into the rete testis of a recipient animal. Recipient genetically modified blastocysts are implanted into pseudopregnant surrogate females. The progeny which have a genetic modification to the germline can then be established, and lines homozygous for the genetic modification can be produced by interbreeding.

In another embodiment, the cytokine gene is mutated in a somatic cell and then used to create a genetically modified animal by somatic cell nuclear transfer. Somatic cell nuclear transfer uses embryonic, fetal, or adult donor cells which are isolated, cultured, and/or modified to establish a cell line. Individual donor cells are fused to an enucleated oocyte. The fused cells are cultured to blastocyst stage, and then transplanted into the uterus of a pseudopregnant female.

In one embodiment, the present invention is directed to methods for mutating a single gene or multiple genes (e.g., two or more) in eukaryotic cells and multicellular organisms. The present invention contemplates several methods for creating mutations in the cytokine gene(s). In one embodiment the mutation is an insertion mutation. In another embodiment the mutation is a deletion mutation. In another embodiment the method of mutation is the introduction of a cassette or gene trap by recombination. In another embodiment a small nucleic acid sequence change is created by mutagenesis (through the creation of frame shifts, stop mutations, substitution mutations, small insertion mutations, small deletion mutations, and the like). In yet another embodiment, a transgene is delivered to knockout or knockdown the products of the cytokine gene (mRNA or protein) in trans.

The invention also is directed to insertional mutagens for making the mutant cells and organisms, and which also can be used to analyze the mutations that are made in the cells and organisms. The invention also is directed to methods in which one or more mutated genes is tagged by a tag provided by the insertional mutagen to allow the detection, selection, isolation, and manipulation of a cell with a genome tagged by the insertional mutagen and allows the identification and isolation of the mutated gene(s). The invention provides methods for making multiple mutations (i.e., mutations in two or more genes that produce a phenotype cumulatively) in cells and organisms and tagging at least one of the mutated genes such that the mutation can be rapidly identified.

The term gene disruption as used herein refers to a gene knock-out or knock-down in which an insertional mutagen is integrated into an endogenous gene thereby resulting expression of a fusion transcript between endogenous exons and sequences in the insertional mutagen.

In one embodiment, the invention provides for insertional mutagenesis involving the integration of one or more polynucleotide sequences into the genome of a cell or organism to mutate one or more endogenous genes in the cell or organism. Thus, the insertional mutagenic polynucleotides of the present invention are designed to mutate one or more endogenous genes when the polynucleotides integrate into the genome of the cell.

Accordingly, the insertional mutagens used in the present invention can comprise any nucleotide sequence capable of altering gene expression levels or activity of a gene product upon insertion into DNA that contains the gene. The insertional mutagens can be any polynucleotide, including DNA and RNA, or hybrids of DNA and RNA, and can be single-stranded or double-stranded, naturally occurring or non-naturally occurring (e.g., phosphorothioate, peptide-nucleic acids, etc.). The insertional mutagens can be of any geometry, including but not limited to linear, circular, coiled, super-coiled, branched, hairpin, and the like, and can be any length capable of facilitating mutation, and tagging of an endogenous gene. In certain embodiments, the insertional mutagens can comprise one or more nucleotide sequences that provide a desired function.

In another embodiment, the method further involves transforming a cell with a nucleic acid construct comprising donor DNA. An example of donor DNA may include a DNA transposon. Transposable elements are discrete sequences in the genome which are mobile. They have the ability to translocate from one position in the genome to another. Unlike most genetic entities that can create modification to an organism's genome, transposons do not require homology with the recipient genome for insertion. Transposons contain inverted terminal repeats which are recognized by the protein transposase. Transposase facilitates the transposition event. Transposition can occur in replicative (the element is duplicated) or nonreplicative (element moves from one site to another and is conserved) mechanism. Transposons can either contain their own transposase or transposase can be added in trans to facilitate transposition. The transposon promotes genetic modifications in many ways. The insertion itself may cause genetic modification by disruption of a DNA sequence or introduction of DNA. The transposon may be used to deliver a gene trap.

In another embodiment, the method for mutagenesis involves transforming a cell with nucleic acid by use of a LTR retrotransposon with reverse transcriptase. The retrotransposon is initially composed of a single strand of RNA. This single stranded RNA is converted into a double stranded DNA by reverse transcriptase. This is a linear duplex of DNA that is integrated into the host's genome by the enzyme integrase. This insertion event is much like a transposition event and can be engineered to genetically modify a host's genome.

In another embodiment, the method for mutagenesis is a non-LTR retrotransposon. Long Interspersed Nucleotide Elements (LINEs) are retrotransposons that do not have long terminal repeats (LTR's). The LINES open reading frame 1 (ORF1) is a DNA binding protein, ORF2 provides both reverse transcriptase and endonuclease activity. The endonucleolytic nick provides the 3'-OH end required for priming the synthesis of cDNA on the RNA template by reverse transcriptase. A second cleavage site opens the other strand of DNA. The RNA/DNA hybrid integrates into the host genome before or after converting into double stranded DNA. The integration process is called target primed reverse transcription (TPRT).

In another embodiment a retrovirus may be used for insertional genetic modification. The retroviral vector (e.g. lentivirus) inserts itself into the genome. The vector can carry a transgene or can be used for insertional mutagenesis. The infected embryos are then injected into a receptive female. The female gives birth to founder animals which have genetic modifications in their germline Genetically modified lines are established with these founder animals.

In another embodiment, mutagenesis by recombination of a cassette into the genome may be facilitated by targeting constructs or homologous recombination vectors. Homologous recombination vectors are composed of fragments of DNA which are homologous to target DNA. Recombination between identical sequences in the vector and chromosomal DNA will result in genetic modification. The vector may also contain a selection method (e.g., antibiotic resistance or GFP) and a unique restriction enzyme site used for further genetic modification. The targeting vector will insert into the genome at a position (e.g., exon, intron, regulatory element) and create genetic modification.

In another embodiment, mutagenesis through recombination of a cassette into the genome may be carried out by Serine and Tyrosine recombinase with the addition of an insertion cassette. Site-specific recombination occurs by recombinase protein recognition of DNA, cleavage and rejoining as a phosphodiesterase bond between the serine or tyrosine residues. A cassette of exogenous or endogenous DNA may be recombined into the serine or tyrosine site. The cassette can contain a transgene, gene trap, reporter gene or other exogenous or endogenous DNA.

In one embodiment, the present invention is directed to methods for both targeted (site-specific) DNA insertions and targeted DNA deletions. In one embodiment, the method involves transformation of a cell with a nucleic acid or mRNA construct minimally comprising DNA encoding a chimeric zinc finger nuclease (ZFN), which can be used to create a DNA deletion. In another embodiment, a second DNA construct can be provided that will serve as a template for repair of the cleavage site by homologous recombination. In this embodiment, a DNA insertion may be created. The DNA insertion may contain a gene trap cassette.

The invention also is directed to nucleic acid sequence mutation for making the mutant cells and organisms.

In one embodiment, the method involves chemical mutagenesis with mutagens such as methane-sulfonic acid ethylester (EMS), N-ethyl-N-nitrosourea (ENU), diepoxyoctane and UV/trimethylpsorlalen to create nucleic acid sequence mutations.

In another embodiment, sequence editing methods are used that involve the delivery of small DNA fragments, hybrid DNA/RNA molecules, and modified DNA polymers to create sequence mismatches and nucleic acid mutations. RNA/DNA hybrids are molecules composed of a central stretch of DNA flanked by short RNA sequences that form hairpin structures. The RNA/DNA hybrids can produce single base-pair substitutions and deletions resulting in nucleotide mutations. Some other sequence editing examples include triplex forming oligonucleotides, small fragment homologous replacement, single-stranded DNA oligonucleotides, and adeno-associated virus (AAV) vectors.

The invention also is directed to genetic expression modification or mutagenesis, which may be carried out by delivery of a transgene that works in trans.

In one embodiment, RNA interference (RNAi) may be used to alter the expression of a gene. Single stranded mRNA can be regulated by the presence of sections of double stranded RNA (dsRNA) or small interfering RNA (siRNA). Both anti-sense and sense RNAs can be effective in inhibiting gene expression. siRNA mediates RNA interference and is created by cleavage of long dsDNA by the enzyme Dicer. RNAi can create genetic modification by triggering the degradation of mRNA's that are complementary to either strand of short dsRNA. When siRNA is associated with complementary single-stranded RNA it can signal for nuclease to degrade the mRNA. RNAi can also result in RNA silencing which occurs when the short dsRNA inhibits expression of a gene. Other forms of inhibitory RNA, such as small hairpin RNA (shRNA) are envisioned.

In another embodiment, the delivery of a transgene encoding a dominant negative protein may alter the expression of a target gene. Dominant negative proteins can inhibit the activity of an endogenous protein. One example is the expression a protein which contains the ligand binding site of an endogenous protein. The expressed dominant-negative protein "soaks up" all of the available ligand. The endogenous protein is therefore not activated, and the wild type function is knocked out or knocked down.

Other schemes based on these general concepts are within the scope and spirit of the invention, and are readily apparent to those skilled in the art.

The invention also provides methods for making homozygous mutations in rats by breeding a genetically modified rat which is heterozygous for a mutant allele with another genetically modified rat which is heterozygous for the same mutant allele. On average 25% of offspring of such matings are expected to produce animals that are homozygous for the mutant allele. Homozygous mutations are useful for discovering functions associated with the mutated gene.

The present invention is directed generally to reduction or inactivation of gene function or gene expression in cells in vitro and in multicellular organisms. The invention encompasses methods for mutating cells using one or more mutagens, particularly wherein at least one mutation is an insertion mutation, a deletion mutation, or a nucleic acid sequence mutation, to achieve a homozygous gene mutation or mutation of multiple genes required cumulatively to achieve a phenotype. The methods are used to create knockouts, knock-downs, and other modifications in the same cell or organism.

The mutation can result in a change in the expression level of a gene or level of activity of a gene product. Activity encompasses all functions of a gene product, e.g. structural, enzymatic, catalytic, allosteric, and signaling. In one embodiment, mutation results in a decrease or elimination of gene expression levels (RNA and/or protein) or a decrease or elimination of gene product activity (RNA and/or protein). Most mutations will decrease the activity of mutated genes. However, both the insertional and physicochemical mutagens can also act to increase or to qualitatively change (e.g., altered substrate on binding specificity, or regulation of protein activity) the activity of the product of the mutated gene. Although mutations will often generate phenotypes that may be difficult to detect, most phenotypically detectable mutations change the level or activity of mutated genes in ways that are deleterious to the cell or organism.

As used herein, decrease means that a given gene has been mutated such that the level of gene expression or level of activity of a gene product in a cell or organism is reduced from that observed in the wild-type or non-mutated cell or organism. This is often accomplished by reducing the amount of mRNA produced from transcription of a gene, or by mutating the mRNA or protein produced from the gene such that the expression product is less abundant or less active.

Disclosed are cells produced by the process of transforming the cell with any of the disclosed nucleic acids. Disclosed are cells produced by the process of transforming the cell with any of the non-naturally occurring disclosed nucleic acids.

Disclosed are any of the disclosed peptides produced by the process of expressing any of the disclosed nucleic acids. Disclosed are any of the non-naturally occurring disclosed peptides produced by the process of expressing any of the disclosed nucleic acids. Disclosed are any of the disclosed peptides produced by the process of expressing any of the non-naturally disclosed nucleic acids.

Disclosed are animals produced by the process of transfecting a cell within the animal with any of the nucleic acid molecules disclosed herein. Disclosed are animals produced by the process of transfecting a cell within the animal any of the nucleic acid molecules disclosed herein, wherein the animal is a rat. Also disclosed are animals produced by the process of transfecting a cell within the animal any of the nucleic acid molecules disclosed herein, wherein the mammal is a rat.

Such methods are used to achieve mutation of a single gene to achieve a desired phenotype as well as mutation of multiple genes, required cumulatively to achieve a desired phenotype, in a rat cell or rat. The invention is also directed to methods of identifying one or more mutated genes, made by the methods of the invention, in rat cells and in rats, by means of a tagging property provided by the insertional mutagen(s). The insertional mutagen thus allows identification of one or more genes that are mutated by insertion of the insertional mutagen.

The invention is also directed to rat cells and rats created by the methods of the invention and uses of the rat cells and rats. The invention is also directed to libraries of rat cells created by the methods of the invention and uses of the libraries.

Cytokine-Cytokine Mediated Autoimmune and Inflammatory Disease-Associated Genes

The invention also features a novel genetically modified rat with a genetically engineered modification in a gene encoding a cytokine-cytokine mediated autoimmune and inflammatory disease associated protein. In another aspect, the invention features a genetically modified rat, wherein a gene encoding cytokine protein is modified resulting in reduced cytokine protein activity. In preferred embodiments of this aspect, the genetically modified rat is homozygous for the modified gene. In other preferred embodiments, the gene encoding cytokine protein is modified by disruption, and the genetically modified rat has reduced cytokine protein activity. In yet another embodiment, the transgenic rat is heterozygous for the gene modification.

In another embodiment of this aspect of the invention, the invention features a nucleic acid vector comprising nucleic acid capable of undergoing homologous recombination with an endogenous cytokine gene in a cell, wherein the homologous recombination results in a modification of the cytokine gene resulting in decreased cytokine protein activity in the cell. In another aspect, the modification of the cytokine gene is a disruption in the coding sequence of the endogenous cytokine gene.

Another embodiment of this aspect of the invention features a rat cell, wherein the endogenous gene encoding cytokine protein is modified, resulting in reduced cytokine protein activity in the cell.

In certain embodiments, the reduced cytokine protein activity is manifested. In a related aspect, the invention features a rat cell containing an endogenous cytokine gene into which there is integrated a transposon comprising DNA encoding a gene trap and/or a selectable marker.

In another aspect, the invention features a rat cell containing an endogenous cytokine gene into which there is integrated a retrotransposon comprising DNA encoding a gene trap and/or a selectable marker. In another aspect, the invention features a rat cell containing an endogenous cytokine gene into which there is DNA comprising an insertion mutation in the cytokine gene. In another aspect, the invention features a rat cell containing an endogenous cytokine gene into which there is DNA comprising a deletion mutation in the cytokine gene. In another aspect, the invention features a rat cell containing an endogenous cytokine gene in which there has been nucleic acid sequence modification of the cytokine gene.

In another embodiment of the invention, the invention features a method for determining whether a compound is potentially useful for treating or alleviating the symptoms of a cytokine gene disorder, which includes (a) providing a cell that produces a cytokine protein, (b) contacting the cell with the compound, and (c) monitoring the activity of the cytokine protein, such that a change in activity in response to the compound indicates that the compound is potentially useful for treating or alleviating the symptoms of a cytokine gene disorder.

It is understood that simultaneous targeting of more than one gene may be utilized for the development of "knock-out rats" (i.e., rats lacking the expression of a targeted gene product), "knock-in rats" (i.e., rats expressing a fusion protein or a protein encoded by a gene exogenous to the targeted locus), "knock down rats" (i.e., rats with a reduced expression of a targeted gene product), or rats with a targeted gene such that a truncated gene product is expressed.

Rat models that have been genetically modified to alter cytokine gene expression may be used in in vivo assays to test for activity of a candidate cytokine modulating agent, or to further assess the role of cytokine gene in a cytokine pathway process such as T lymphocyte mediated apoptosis or native DNA autoantibody production. Preferably, the altered cytokine gene expression results in a detectable phenotype, such as altered levels of T-, B-, and Natural Killer (NK)-cells, impaired macrophage and immunoglobulin function, or increases in susceptibility to autoimmune diseases compared to control animals having normal cytokine gene expression. The genetically modified rat may additionally have altered cytokine gene expression (e.g. cytokine gene knockout). In one embodiment, the genetically modified rats are genetically modified animals having a heterologous nucleic acid sequence present as an extrachromosomal element in a portion of its cells, i.e. mosaic animals (see, for example, techniques described by Jakobovits, 1994, Curr. Biol. 4:761-763) or stably integrated into its germ line DNA (i.e., in the genomic sequence of most or all of its cells). Heterologous nucleic acid is introduced into the germ line of such genetically modified animals by genetic manipulation of, for example, embryos or germ cells or germ cells precursors of the host animal.

Methods of making genetically modified rodents are well-known in the art (see Brinster et al., Proc. Nat. Acad. Sci. USA 82: 4438-4442 (1985), U.S. Pat. Nos. 4,736,866 and 4,870,009, both by Leder et al., U.S. Pat. No. 4,873,191 by Wagner et al., and Hogan, B., Manipulating the Mouse Embryo, Cold Spring Harbor Laboratory Press, Cold Spring Harbor, N.Y., (1986); for particle bombardment see U.S. Pat. No. 4,945,050, by Sandford et al.; for genetically modified Drosophila see Rubin and Spradling, Science (1982) 218:348-53 and U.S. Pat. No. 4,670,388; for genetically modified insects see Berghammer A. J. et al., A Universal Marker for Genetically modified Insects (1999) Nature 402:370-371; for genetically modified zebrafish see Lin S., Genetically modified Zebrafish, Methods Mol Biol. (2000); 136:375-3830); for microinjection procedures for fish, amphibian eggs and birds see Houdebine and Chourrout, Experientia (1991) 47:897-905; Hammer et al., Cell (1990) 63:1099-1112; and for culturing of embryonic stem (ES) cells and the subsequent production of genetically modified animals by the introduction of DNA into ES cells using methods such as electroporation, calcium phosphate/DNA precipitation and direct injection see, e.g., Teratocarcinomas and Embryonic Stem Cells, A Practical Approach, E. J. Robertson, ed., IRL Press (1987)). Clones of the nonhuman genetically modified animals can be produced according to available methods (see Wilmut, I. et al.

(1997) Nature 385:810-813; and PCT International Publication Nos. WO 97/07668 and WO 97/07669).

In one embodiment, the genetically modified rat is a "knock-out" animal having a heterozygous or homozygous alteration in the sequence of an endogenous cytokine gene that results in a dysregulation of immune function, preferably such that cytokine gene expression is undetectable or insignificant. Knock-out animals are typically generated by homologous recombination with a vector comprising a transgene having at least a portion of the gene to be knocked out. Typically a deletion, addition or substitution has been introduced into the transgene to functionally disrupt it. The transgene can be a human gene (e.g., from a human genomic clone) but more preferably is an ortholog of the human gene derived from the genetically modified host species. For example, a mouse cytokine gene is used to construct a homologous recombination vector suitable for altering an endogenous cytokine gene in the mouse genome. Detailed methodologies for homologous recombination in rodents are available (see Capecchi, Science (1989) 244:1288-1292; Joyner et al., Nature (1989) 338:153-156). Procedures for the production of non-rodent genetically modified mammals and other animals are also available (Houdebine and Chourrout, supra; Pursel et al., Science (1989) 244:1281-1288; Simms et al., Bio/Technology (1988) 6:179-183). In a preferred embodiment, knock-out animals, such as rats harboring a knockout of a specific gene, may be used to produce antibodies against the human counterpart of the gene that has been knocked out (Claesson M H et al., (1994) Scan J Immunol 40:257-264; Declerck P J et al., (1995) J Biol Chem. 270:8397-400).

In another embodiment, the genetically modified rat is a "knock-down" animal having an alteration in its genome that results in altered expression (e.g., decreased expression) of the cytokine gene, e.g., by introduction of mutations to the cytokine gene, or by operatively inserting a regulatory sequence that provides for altered expression of an endogenous copy of the cytokine gene.

Genetically modified rats can also be produced that contain selected systems allowing for regulated expression of the transgene. One example of such a system that may be produced is the cre/loxP recombinase system of bacteriophage P1 (Lakso et al., PNAS (1992) 89:6232-6236; U.S. Pat. No. 4,959,317). If a cre/loxP recombinase system is used to regulate expression of the transgene, animals containing transgenes encoding both the Cre recombinase and a selected protein are required. Such animals can be provided through the construction of "double" genetically modified animals, e.g., by mating two genetically modified animals, one containing a transgene encoding a selected protein and the other containing a transgene encoding a recombinase. Another example of a recombinase system is the FLP recombinase system of Saccharomyces cerevisiae (O'Gorman et al. (1991) Science 251:1351-1355; U.S. Pat. No. 5,654,182). In a preferred embodiment, both Cre-LoxP and Flp-Frt are used in the same system to regulate expression of the transgene, and for sequential deletion of vector sequences in the same cell (Sun X et al (2000) Nat Genet 25:83-6).

The genetically modified rats can be used in genetic studies to further elucidate the cytokine function pathways, as animal models of disease and disorders implicating dysregulated cytokine function, and for in vivo testing of candidate therapeutic agents, such as those identified in screens described below. The candidate therapeutic agents are administered to a genetically modified animal having altered cytokine pathway and phenotypic changes are compared with appropriate control animals such as genetically modified animals that receive placebo treatment, and/or animals with unaltered cytokine pathways that receive candidate therapeutic agent.

The invention also features novel genetically modified animals with a genetically engineered modification in the gene encoding cytokine-cytokine signaling proteins. In one aspect, the invention features a genetically modified non-human mammal, wherein a gene encoding cytokine-cytokine signaling gene is provided as follows:

Cytokine-cytokine signaling, apoptosis, cytotoxic T-cell mediated death: Faslg & Fas.

The Faslg gene encodes a cytokine ligand which binds to the cell surface of the Fas receptor. The cytokine-cytokine signaling interaction between the ligand and receptor mediates T-cell apoptosis. Cells that are not necessary or toxic are removed by this process. Senescent cells are able to be removed by apoptosis and replaced by new cells. When Faslg binds to Fas in activated T-lymphocytes, it enables cytotoxic activity. The Faslg-Fas system is essential for abolishing peripheral T lymphocytes and activation induced suicide of mature T-cells. Faslg-Fas cytokine signal transduction is also involved in the development of mature T-cells. The inability of Faslg−/− & Fas−/− mice to mediate Faslg-Fas induced cell death results in a complex immunologic disorder accompanied by defects in the B and T lymphoid compartments. This disorder results in severe chronic inflammation and autoimmune responses to native elements. Systemic Lupus Erythematosus (SLE) with autoimmunity is exhibited in mouse models which have mutations in the Faslg-Fas ligand-receptor mediated cytokine signaling pathway. In humans with defects to the Faslg-Fas cytokine signaling pathway a decrease in activation of induced cell death, and an increase in proliferation of T-cell activation results in a disease known as Autoimmune Lymphoproliferative Syndrome (ALPS). Some clinical features of ALPS include but are not limited to, autoimmune hemolytic anemia, T-cell hyperplasia, thrombocytopenia, peripheral lymphadenopathy, hepatomegaly, hypergammaglobulinemia, renal insufficiency, and recurrent infections. When the blood is examined from ALPS patients they exhibit an extreme increase in the number of B lymphocytes, and mature CD3+, CD4−, CD8− T-lymphocytes. The disease progression of ALSP is attributed to disruptions in the Faslg-Fas cytokine-cytokine signaling path which results in the inability to mediate cytotoxic T-cell death. The consequence of a disruption in this component of the cytokine-cytokine signaling pathway is uncontrolled mature lymphocyte proliferation, chronic inflammation and enhanced autoimmune response.

Interferon-gamma (IFN-γ), cytokine-cytokine signaling and macrophage immunomodulatory defects.

Interferon-gamma (IFN-γ) is a cytokine that is secreted by activated T-cells and Natural Killer (NK) cells. IFN-γ is required for proper intuitive immunity via activation of non-specific macrophages. IFN-γ is also immersed in adaptive immunity against viral and bacterial infections by introduction of major histocompatability complex (MHC) class II antigen on macrophage surfaces, and macrophage production of nitric oxide. IFN-γ regulates activation of T lymphocytes, NK cell cytolytic activity, and is involved in various immunomodulatory effects. In mice which are defective of IFN-γ a number of cytokine-cytokine signal activated events are disrupted. The mice produce little macrophage nitric oxide and MHC class II when infected by bacterial pathogens. The mice exhibit enhanced proliferation of T-cells in the spleen, and have lower cytolytic activity of splenic NK cells. These phenotypes and others in IFN-γ−/− mice provide an important model of cytokine-cytokine signaling derived studies of immunological, autoinflammatory and autoimmune diseases.

IFN-γ is also an important mediator of tumor regression. Mice which are defective of IFN-γ are excellent models for allograft tumor regression. Humans with defects in IFN-γ results in multiple autoinflammatory and autoimmune diseases. A common autoimmune disease which attributed to defects in IFN-γ is Rheumatoid Arthritis (RA). RA is an inflammatory disease of the joints which exhibit an enhanced autoimmune response. Patients with defects in IFN-γ also display immunological disease susceptibility. IFN-γ defects are involved in Mycobacterium tuberculosis infections, Acquired Immunodeficiency Syndrome (AIDS), and Hepatitis C virus susceptibility. Patients with IFN-γ mutations are susceptible to Aplastic Anemia due to the genes involvement in tumor regression.

Tumor Necrosis Factor alpha (TNF-α) cytokine-cytokine signaling, immune follicular dendrite cell (FDC) networks, and contact hypersensitivity.

TNF-α is a proinflammatory cytokine stimuli-secreted by T-cells and macrophages. Mice that lack TNF-α function readily succumb to *L. monocytogenes* infections, and show reduced hypersensitivity responses. Yet these mice are resistant to lipopolysaccharides (LPS) systemic toxicity. Furthermore, TNF-α–/– mice lack splenic B-cell follicles and are defective in organized FDC networks. In human, inflammatory cytokines such as TNF-α are implicated in the pathogenesis of chronic inflammatory diseases such as Psoriasis. The development of Psoriasis is a direct result of cytokine-cytokine signaling of TNF-α leading to enhanced activation and proliferation of resident T-cells. A classic example of how modification of the cytokine-cytokine pathway results in complex autoimmune and chronic inflammatory diseases is the case of TNF-α and Rheumatoid Arthritis (RA). Overproduction of TNF-α denies CD4+/CD25+ regulatory T-cells of RA patients the ability to suppress proinflammatory cytokine production by CD4+/CD25– T-cells.

Interleukin 2 (IL-2), cytokine-cytokine signaling, suppression of proinflammatory cytokines and immune homeostasis.

IL-2 is an immune-regulatory lymphokine produced in mature T lymphocytes by lectin or is antigen activated. The IL-2 plays an important role in T-cell differentiation and over-expression results in augmented NK cell activity. Mice deficient of IL-2 display reduced T-cell responses and exhibit dramatic variations in serum immunoglobulin levels. Alleles that control susceptibility or resistance to human autoimmune diseases correlate with IL-2 differential expression. When IL-2 is mutated in autoimmune disease patients it triggers a dysregulation in the cytokine-cytokine signaling pathway. This dysregulation leads to a reduction of CD4+/CD25+ regulatory T-cells that are critical for the suppression of proinflammatory cytokines and immune homeostasis.

Interleukin 10 (IL-10), cytokine-cytokine signaling, macrophage suppression, and inhibition of inflammation.

IL-10 is an immune regulatory cytokine that is secreted upon stimulation by T helper cell subset 2 (Th2), Ly-1B cells, macrophages, thymocytes, and keratinocytes. IL-10 also enhances expression of major histocompatibility complex (MHC) class II molecules. IL-10 is a cogent suppressor of macrophage activation. IL-10 inhibits the production of proinflammatory cytokines IL-1, IL-6, TNF-α, which are stimulated by LPS and IFN-γ. The modification of IL-10 involvement in the cytokine-cytokine signaling pathway leads to the overproduction or suppression of cytokine proinflammatory reactions. IL-10–/– mice suffer from chronic enterocolitis; which in humans is characterized by inflammatory swelling of the abdomen. IL-10 deficient mice also exhibit mucosal hyperplasia, inflammatory reactions, and an increased expression of MHC class II molecules. Since IFN-γ is critical for synthesis of nitric oxide involved in parasite resistance; IFN-γ suppression by IL-10 results in a decrease resistance to parasites. When the IL-10 cytokine signaling pathway is disrupted in humans the increases in macrophage produced pro-inflammatory cytokines results in chronic inflammatory and autoimmune diseases such as Rheumatoid Arthritis (RA). The decrease in IFN-γ production of nitric oxide, and MHC class I molecules results in an increased susceptibility to parasitic infections.

Interleukin 12 (IL-12), cytokine-cytokine signaling, IFN-γ deficiency, Type 1 & 2 T helper cell regulation and cell mediated immunity.

IL-12 is exclusive among cytokines as it consists of two disulfide-bonded units called p35 and p40. Both subunits are essential for IL-12 function. IL-12 is synthesized by macrophages, monocytes, dendrite cells and other antigen-presenting cells. IL-12 is a multifactorial effector of T and NK cells. IL-12 is a T and NK growth factor, induces IFNγ secretion, enhances the lytic activity of NK and lymphokine activated killer (LAK) cells, and produces cytolytic T lymphocyte (CTL) responses. IL-12 also plays an important role in regulating Type 1 (Th1) and Type 2 (Th2) helper T cells. Th1 cells produce IFNγ and IL-2; which are cytokines that establish primary cellular immunity. Th2 cells produce 11-4, 5, 10 & 13. When IL-12 cytokine signaling is disrupted in mouse models it results in reduction of IFNγ, and Th1 cell production. In contrast IL-12–/– mice display enhanced Th2 production in cytokines such as IL-4. Delayed type hypersensitivity (DTH) reactions were deficient in IL-12–/– mice. IL-12 deficient mice exhibit a phenotype that corresponds to a form of cytokine-cytokine signaling pathway modification; IFNγ production is reduced, Th1/Th2 regulation is disproportional, and cytokine DTH responses are suppressed.

The invention also features novel genetically modified cells and animals with a genetically engineered modification in a gene encoding cytokine-cytokine signaling proteins. In one aspect, the invention features genetically modified rat cells or rats, wherein a gene modification occurs in a gene encoding a cytokine-cytokine signaling protein provided in Table 1:

TABLE 1

| Cytokine gene | Function | Rat Chromosomal Location |
|---|---|---|
| Faslg | The ligand for Fas. Interaction of Fas with Faslg is essential in the mediation of apoptosis cell types such as lymphocytes. Also known as FASL; CD178; CD95L; CD95-L; TNFSF6; APT1LG1; FASLG. | 13q22 |
| Fas | Physiological regulator of programmed cell death and regulation in the immune system. Fas-Faslg interaction forms a death inducing signaling complex. | 1q52 |
| IFN-γ | Critical for innate and viral/bacterial adaptive immunity, and is also involved in tumor control. | 7q22 |
| TNF-α | Proinflammatory cytokine involved in regulation of cell proliferation, differentiation, apoptosis, lipid metabolism, and coagulation. | 20p12 |
| IL-2 Prkdc | Proliferation of T and B lymphocytes, essential for immune response to antigenic stimuli. | 2q25 |
| Il-10 | Down-regulation of Th1 cytokines, MHC class II Ags, and co-stimulatory molecules on macrophages, enhancement of B cell survival, proliferation, and antibody production, blocks NF-kappa B | 13q13 |

TABLE 1-continued

| Cytokine gene | Function | Rat Chromosomal Location |
|---|---|---|
| | activity, regulation of the JAK-STAT signaling pathway. | |
| IL-12a | Required for T-cell independent induction of IFN-γ, and is critical for differentiation of Th1 and Th2. | 2q31 |

Methods

The methods used in the present invention are comprised of a combination of genetic introduction methods, genetic modification or mutagenesis mechanisms, and vector delivery methods. For all genetic modification or mutagenesis mechanisms one or more introduction and delivery method may be employed. The invention may include but is not limited to the methods described below.

Genetic Introduction Methods

In one introduction method, the cytokine gene is mutated directly in the germ cells of an adult animal. This method usually involves the creation of a transgenic founder animal by pronuclear injection. Rat oocytes are microinjected with DNA into the male pronucleus before nuclear fusion. The microinjected DNA creates a transgenic founder rat. In this method, a female rat is mated and the fertilized eggs are flushed from their oviducts. After entry of the sperm into the egg, the male and female pronuclei are separate entities until nuclear fusion occurs. The male pronucleus is larger are can be identified via dissecting microscope. The egg can be held in place by micromanipulation using a holding pipette. The male pronucleus is then microinjected with DNA that can be genetically modified. The microinjected eggs are then implanted into a surrogate pseudopregnant female which was mated with a vasectomized male for uterus preparation. The foster mother gives birth to transgenic founder animals. If the transgenic DNA encodes the appropriate components of a mutagenesis system, such as transposase and a DNA transposon, then mutagenesis will occur directly in the germ cells of founder animals and some offspring will contain new mutations. Chemical mutagenesis can also be used to cause direct germ line mutations.

In another introduction method, the cytokine gene is mutated in the early embryo of a developing animal. The mutant embryonic cells develop to constitute the germ cells of the organism, thereby creating a stable and heritable mutation. Several forms of mutagenesis mechanisms can be introduced this way including, but not limited to, zinc finger nucleases and delivery of gene traps by a retrovirus.

In another introduction method, the cytokine gene is mutated in a pluripotent cell. These pluripotent cells can proliferate in cell culture and be genetically modified without affecting their ability to differentiate into other cell types including germ line cells. Genetically modified pluripotent cells from a donor can be microinjected into a recipient blastocyst, or in the case of spermatogonial stem cells can be injected into the rete testis of a recipient animal. Recipient genetically modified blastocysts are implanted into pseudopregnant surrogate females. The progeny which have a genetic modification to the germ line can then be established, and lines homozygous for the genetic modification can be produced by interbreeding.

In another introduction method, the cytokine gene is mutated in a somatic cell and then used to create a genetically modified animal by somatic cell nuclear transfer. Somatic cell nuclear transfer uses embryonic, fetal, or adult donor cells which are isolated, cultured, and/or modified to establish a cell line. Individual donor cells are fused to an enucleated oocyte. The fused cells are cultured to blastocyst stage, and then transplanted into the uterus of a pseudopregnant female. Alternatively the nucleus of the donor cell can be injected directly into the enucleated oocyte. See U.S. Appl. Publ. No. 20070209083.

Genetic Modification Methods

Mobile DNA Technology

DNA transposons are discrete mobile DNA segments that are common constituents of plasmid, virus, and bacterial chromosomes. These elements are detected by their ability to transpose self-encoded phenotypic traits from one replicon to another, or to transpose into a known gene and inactivate it. Transposons, or transposable elements, include a piece of nucleic acid bounded by repeat sequences. Active transposons encode enzymes (transposases) that facilitate the insertion of the nucleic acid into DNA sequences.

The lifecycle and insertional mutagenesis of DNA transposon Sleeping Beauty (SB) is depicted in FIG. 1. In its lifecycle, the SB encodes a transposase protein. That transposase recognizes the inverted terminal repeats (ITRs) that flank the SB transposon. The transposase then excises SB and reintegrates it into another region of the genome. Mutagenesis via Sleeping Beauty is depicted. The mechanism is similar to the life cycle, but transposase is not encoded by the transposon, but instead is encoded elsewhere in the genome The Sleeping Beauty (SB) mutagenesis breeding and screening scheme is depicted in FIG. 2. One rat referred to as the "driver" rat contains the (SB) transposase within its genome. A second rat, the "donor" rat contains the transposon which has the transposase-recognizable inverted terminal repeats (ITRs). The two rats are bred to create the "seed" rat which has an active transposon containing transposase and ITRs. The transposon recognizes the ITRs, excises the transposon, and inserts it elsewhere in the rat's genome. This insertion event often disrupts coding, regulatory, and other functional regions in the genome to create knockout rat models. The "seed" rat is bred with wild type rats which beget heterozygous G1 mutants. If the transposon has inserted into the genome, the event will be recorded via size comparison of DNA by Southern blot analysis. The exact location of the transposon insertion is determined by PCR-based amplification methods combined with sequencing of the DNA flanking the new insertion.

The sequences for the DNA transposons Sleeping Beauty (SB) piggyBac (PB) functional domains are shown in FIG. 3. The SB and PB transposase sequences encode the protein that recognizes the ITRs and carries out the excision and re-integration. The 3' and 5' ITRs are the flanking sequences which the respective transposases recognizes in order to carry out excision and reintegration elsewhere in the genome.

The DNA transposon Sleeping Beauty (SB) was used by the inventors to create a knockout rat in the Faslg gene. The mechanism is depicted in FIG. 4, and is the same as that described above. The transposase is encoded, and the protein recognizes the ITRs of the transposon. The transposon is then excised and reinserted into the first intron of the rat Faslg gene which resides on chromosome 13, location 13q22.

In another embodiment, the present invention utilizes the transposon piggyBac, and sequence configurations outside of piggyBac, for use as a mobile genetic element as described in U.S. Pat. No. 6,962,810. The Lepidopteran transposon piggyBac is capable of moving within the genomes of a wide variety of species, and is gaining prominence as a useful gene transduction vector. The transposon structure includes a complex repeat configuration consisting of an internal repeat (IR), a spacer, and a terminal repeat (TR) at both ends, and a single open reading frame encoding a transposase.

The Lepidopteran transposable element piggyBac transposes via a unique cut-and-paste mechanism, inserting exclusively at 5' TTAA 3' target sites that are duplicated upon insertion, and excising precisely, leaving no footprint (Elick et al., 1996b; Fraser et al., 1996; Wang and Fraser 1993).

In another embodiment, the present invention utilizes the Sleeping Beauty transposon system for genome manipulation as described, for example, in U.S. Pat. No. 7,148,203. In one embodiment, the system utilizes synthetic, salmonid-type Tc1-like transposases with recognition sites that facilitate transposition. The transposase binds to two binding-sites within the inverted repeats of salmonid elements, and appears to be substrate-specific, which could prevent cross-mobilization between closely related subfamilies of fish elements.

In another aspect of this invention, the invention relates to a transposon gene transfer system to introduce DNA into the DNA of a cell comprising: a nucleic acid fragment comprising a nucleic acid sequence positioned between at least two inverted repeats wherein the inverted repeats can bind to a SB protein and wherein the nucleic acid fragment is capable of integrating into DNA of a cell; and a transposase or nucleic acid encoding a transposase. In one embodiment, the transposase is provided to the cell as a protein and in another the transposase is provided to the cell as nucleic acid. In one embodiment the nucleic acid is RNA and in another the nucleic acid is DNA. In yet another embodiment, the nucleic acid encoding the transposase is integrated into the genome of the cell. The nucleic acid fragment can be part of a plasmid or a recombinant viral vector. Preferably, the nucleic acid sequence comprises at least a portion of an open reading frame and also preferably, the nucleic acid sequence comprises at least a regulatory region of a gene. In one embodiment the regulatory region is a transcriptional regulatory region and the regulatory region is selected from the group consisting of a promoter, an enhancer, a silencer, a locus-control region, and a border element. In another embodiment, the nucleic acid sequence comprises a promoter operably linked to at least a portion of an open reading frame.

In the transgene flanked by the terminal repeats, the terminal repeats can be derived from one or more known transposons. Examples of transposons include, but are not limited to the following: Sleeping Beauty (Izsvak Z, Ivies Z. and Plasterk R H. (2000) Sleeping Beauty, a wide host-range transposon vector for genetic transformation in vertebrates. J. Mol. Biol. 302:93-102), mos1 (Bessereau J L, et al. (2001) Mobilization of a Drosophila transposon in the *Caenorhabditis elegans* germ line. Nature. 413(6851):70-4; Zhang L, et al. (2001) DNA-binding activity and subunit interaction of the mariner transposase. Nucleic Acids Res. 29(17):3566-75, piggyBac (Tamura T. et al. Germ line transformation of the silkworm *Bombyx mori* L. using a piggyBac transposon-derived vector. Nat Biotechnol. 2000 January; 18(1):81-4), Himar1 (Lampe D J, et al. (1998) Factors affecting transposition of the Himar1 mariner transposon in vitro. Genetics. 149(11):179-87), Hermes, Tol2 element, Pokey, Tn5 (Bhasin A, et al. (2000) Characterization of a Tn5 pre-cleavage synaptic complex. J Mol Biol 302:49-63), Tn7 (Kuduvalli P N, Rao J E, Craig N L. (2001) Target DNA structure plays a critical role in Tn7 transposition. EMBO J 20:924-932), Tn916 (Marra D, Scott J R. (1999) Regulation of excision of the conjugative transposon Tn916. Mol Microbiol 2:609-621), Tc1/mariner (Izsvak Z, Ivies Z4 Hackett P B. (1995) Characterization of a Tc1-like transposable element in zebrafish (*Danio rerio*). Mol. Gen. Genet. 247:312-322), Minos and S elements (Franz G and Savakis C. (1991) Minos, a new transposable element from *Drosophila hydei*, is a member of the Tc1-like family of transposons. Nucl. Acids Res. 19:6646; Merriman P J, Grimes C D, Ambroziak J, Hackett D A, Skinner P, and Simmons M J. (1995) S elements: a family of Tc1-like transposons in the genome of *Drosophila melanogaster*. Genetics 141:1425-1438), Quetzal elements (Ke Z, Grossman G L, Cornel A J, Collins F H. (1996) Quetzal: a transposon of the Tc1 family in the mosquito *Anopheles albimanus*. Genetica 98:141-147); Txr elements (Lam W L, Seo P, Robison K, Virk S, and Gilbert W. (1996) Discovery of amphibian Tc1-like transposon families. J Mol Biol 257:359-366), Tc1-like transposon subfamilies (Ivies Z, Izsvak Z, Minter A, Hackett P B. (1996) Identification of functional domains and evolution of Tc1-like transposable elements. Proc. Natl. Acad Sci USA 93: 5008-5013), Tc3 (Tu Z. Shao H. (2002) Intra- and inter-specific diversity of Tc-3 like transposons in nematodes and insects and implications for their evolution and transposition. Gene 282:133-142), ICESt1 (Burrus V et al. (2002) The ICESt1 element of *Streptococcus thermophilus* belongs to a large family of integrative and conjugative elements that exchange modules and change their specificity of integration. Plasmid. 48(2): 77-97), maT, and P-element (Rubin G M and Spradling A C. (1983) Vectors for P element-mediated gene transfer in Drosophila. Nucleic Acids Res. 11:6341-6351). These references are incorporated herein by reference in their entirety for their teaching of the sequences and uses of transposons and transposon ITRs.

Translocation of Sleeping Beauty (SB) transposon requires specific binding of SB transposase to inverted terminal repeats (ITRs) of about 230 bp at each end of the transposon, which is followed by a cut-and-paste transfer of the transposon into a target DNA sequence. The ITRs contain two imperfect direct repeats (DRs) of about 32 bp. The outer DRs are at the extreme ends of the transposon whereas the inner DRs are located inside the transposon, 165-166 bp from the outer DRs. Cui et al. (J. Mol Biol 318:1221-1235) investigated the roles of the DR elements in transposition. Within the 1286-bp element, the essential regions are contained in the intervals bounded by coordinates 229-586, 735-765, and 939-1066, numbering in base pairs from the extreme 5' end of the element. These regions may contain sequences that are either necessary for transposase binding or needed to maintain proper spacing between binding sites.

Transposons are bracketed by terminal inverted repeats that contain binding sites for the transposase. Elements of the IR/R subgroup of the Tc1/mariner superfamily have a pair of transposase-binding sites at the ends of the 200-250 bp long inverted repeats (IRs) (Izsvak, et al. 1995). The binding sites contain short, 15-20 bp direct repeats (DRs). This characteristic structure can be found in several elements from evolutionarily distant species, such as Minos and S elements in flies (Franz and Savakis, 1991; Merriman et al, 1995), Quetzal elements in mosquitoes (Ke et al, 1996), Txr elements in frogs (Lam et al, 1996) and at least three Tc1-like transposon subfamilies in fish (Ivies et al., 1996), including SB [Sleeping Beauty] and are herein incorporated by reference.

Whereas Tc1 transposons require one binding site for their transposase in each IR, Sleeping Beauty requires two direct repeat (DR) binding sites within each IR, and is therefore classified with Tc3 in an IR/DR subgroup of the Tc1/mariner superfamily (96,97). Sleeping Beauty transposes into TA dinucleotide sites and leaves the Tc1/mariner characteristic footprint, i.e., duplication of the TA, upon excision. The non-viral plasmid vector contains the transgene that is flanked by IR/DR sequences, which act as the binding sites for the transposase. The catalytically active transposase may be expressed from a separate (trans) or same (cis) plasmid system. The transposase binds to the IR/DRs, catalyzes the excision of the flanked transgene, and mediates its integration into the target host genome.

Naturally occurring mobile genetic elements, known as retrotransposons, are also candidates for gene transfer vehicles. This mutagenesis method generally involves the delivery of a gene trap.

Retrotransposons are naturally occurring DNA elements which are found in cells from almost all species of animals, plants and bacteria which have been examined to date. They are capable of being expressed in cells, can be reverse transcribed into an extrachromosomal element and reintegrate into another site in the same genome from which they originated.

Retrotransposons may be grouped into two classes, the retrovirus-like LTR retrotransposons, and the non-LTR elements such as human L1 elements, Neurospora TAD elements (Kinsey, 1990, Genetics 126:317-326), I factors from Drosophila (Bucheton et al., 1984, Cell 38:153-163), and R2Bm from *Bombyx mori* (Luan et al., 1993, Cell 72: 595-605). These two types of retrotransposon are structurally different and also retrotranspose using radically different mechanisms.

Unlike the LTR retrotransposons, non-LTR elements (also called polyA elements) lack LTRs and instead end with polyA or A-rich sequences. The LTR retrotransposition mechanism is relatively well-understood; in contrast, the mechanism of retrotransposition by non-LTR retrotransposons has just begun to be elucidated (Luan and Eickbush, 1995, Mol. Cell. Biol. 15:3882-3891; Luan et al., 1993, Cell 72:595-605). Non-LTR retrotransposons can be subdivided into sequence-specific and non-sequence-specific types. L1 is of the latter type being found to be inserted in a scattered manner in all human, mouse and other mammalian chromosomes.

Some human L1 elements (also known as a LINEs) can retrotranspose (express, cleave their target site, and reverse transcribe their own RNA using the cleaved target site as a primer) into new sites in the human genome, leading to genetic disorders.

Further included in the invention are DNAs which are useful for the generation of mutations in a cell. The mutations created are useful for assessing the frequency with which selected cells undergo insertional mutagenesis for the generation of genetically modified animals and the like. Engineered L1 elements can also be used as retrotransposon mutagens. Sequences can be introduced into the L1 that increases its mutagenic potential or facilitates the cloning of the interrupted gene. DNA sequences useful for this application of the invention include marker DNAs, such as GFP, that are specifically engineered to integrate into genomic DNA at sites which are near to the endogenous genes of the host organism. Other potentially useful DNAs for delivery are regulatory DNA elements, such as promoter sequences, enhancer sequences, retroviral LTR elements and repressors and silencers. In addition, genes which are developmentally regulated are useful in the invention.

Viral Mutagenesis Methods

Viral vectors are often created using a replication defective virus vector with a genome that is partially replaced by the genetic material of interest (e.g., gene trap, selectable marker, and/or a therapeutic gene). The viral vector is produced by using a helper virus to provide some of the viral components that were deleted in the replication defective virus, which results in an infectious recombinant virus whose genome encodes the genetic material of interest. Viral vectors can be used to introduce an insertion mutation into the rat's genome. Integration of the viral genetic material is often carried out by the viral enzyme integrase. Integrase brings the ends of viral DNA together and converts the blunt ends into recessed ends. Integrase creates staggered ends on chromosomal DNA. The recessed ends of the viral DNA are then joined with the overhangs of genomic DNA, and the single-stranded regions are repaired by cellular mechanisms. Some recombinant virus vectors are equipped with cell uptake, endosomal escape, nuclear import, and expression mechanisms allowing the genetic material of interest to be inserted and expressed in the rat's genome. The genetic material introduced via viral vectors can genetically modify the rat's genome but is not limited to disrupting a gene, inserting a gene to be expressed, and by delivery of interfering RNA. Viral vectors can be used in multiple methods of delivery. The most common mode of delivery is the microinjection of a replication deficient viral vector (e.g. retroviral, adenoviral) into an early embryo (1-4 day) or a one cell pronuclear egg. After viral vector delivery, the embryo is cultured in vitro and transferred to recipient rats to create genetically modified progeny.

In one embodiment, insertion mutations can be created by delivery of a gene trap vector into the rat genome. The gene trap vector consists of a cassette that contains selectable reporter tags. Upstream from this cassette is a 3' splice acceptor sequence. Downstream from the cassette lays a termination sequence poly adenine repeat tail (polyA). The splice accepter sequence allows the gene trap vector to be spliced into chromosomal mRNA. The polyA tail signals the premature interruption of the transcription. The result is a truncated mRNA molecule that has decreased function or is completely non-functional. The gene trap method can also be utilized to introduce exogenous DNA into the genome.

In another embodiment an enhancer trap is used for insertional mutagenesis. An enhancer trap is a transposable element vector that carries a weak minimal promoter which controls a reporter gene. When the transposable element is inserted the promoter drives expression of the reporter gene. The expression of the reporter gene also displays the expression patterns of endogenous genes. Enhancer trapping results in genetic modification and can be used for gain-of-function genetics. The Gal4-mediated expression system is an example of an enhancer trap.

Further included are one or more selectable marker genes. Examples of suitable prokaryotic marker genes include, but are not limited to, the ampicillin resistance gene, the kanamycin resistance gene, the gene encoding resistance to chloramphenicol, the lacZ gene and the like. Examples of suitable eukaryotic marker genes include, but are not limited to, the hygromycin resistance gene, the green fluorescent protein (GFP) gene, the neomycin resistance gene, the zeomycin gene, modified cell surface receptors, the extracellular portion of the IgG receptor, composite markers such as betageo (a lac/neo fusion) and the like.

In one embodiment, the gene trap will need to be integrated into the host genome and an integrating enzyme is needed. Integrating enzymes can be any enzyme with integrating capabilities. Such enzymes are well known in the art and can include but are not limited to transposases, integrases, recombinases, including but not limited to tyrosine site-specific recombinases and other site-specific recombinases (e.g., cre), bacteriophage integrases, retrotransposases, and retroviral integrases.

The integrating enzymes of the present invention can be any enzyme with integrating capabilities. Such enzymes are well known in the art and can include but are not limited to transposases (especially DDE transposases), integrases, tyrosine site-specific recombinases and other site-specific recombinases (e.g., cre), bacteriophage integrases, integrons, retrotransposases, retroviral integrases and terminases.

Disclosed are compositions, wherein the integrating enzyme is a transposase. It is understood and herein contemplated that the transposase of the composition is not limited and to any one transposase and can be selected from at least the group consisting of Sleeping Beauty (SB), Tn7, Tn5, mos1, piggyBac, Himar1, Hermes, Tol2, Pokey, Minos, S elements, P-elements, ICESt1, Quetzal elements, Tn916, maT, Tc1/mariner and Tc3.

Where the integrating enzyme is a transposase, it is understood that the transposase of the composition is not limited and to any one transposase and can be selected from at least the group consisting of Sleeping Beauty (SB), Tn7, Tn5, Tn916, Tc1/mariner, Minos and S elements, Quetzal elements, Txr elements, maT, mos1, piggyBac, Himar1, Hermes, Tol2, Pokey, P-elements, and Tc3. Additional transposases may be found throughout the art, for example, U.S. Pat. No. 6,225,121, U.S. Pat. No. 6,218,185 U.S. Pat. No. 5,792,924 U.S. Pat. No. 5,719,055, U.S. Patent Application No. 20020028513, and U.S. Patent Application No. 20020016975 and are herein incorporated by reference in their entirety. Since the applicable principal of the invention remains the same, the compositions of the invention can include transposases not yet identified.

Also disclosed are integrating enzymes of the disclosed compositions wherein the enzyme is an integrase. For example, the integrating enzyme can be a bacteriophage integrase. Such integrase can include any bacteriophage integrase and can include but is not limited to lamda bacteriophage and mu bacteriophage, as well as Hong Kong 022 (Cheng Q., et al. Specificity determinants for bacteriophage Hong Kong 022 integrase: analysis of mutants with relaxed core-binding specificities. (2000) Mol Microbiol. 36(2):424-36.), HP1 (Hickman, A. B., et al. (1997). Molecular organization in site-specific recombination: The catalytic domain of bacteriophage HP1 integrase at 2.7 A resolution. Cell 89: 227-237), P4 (Shoemaker, N B, et al. (1996). The Bacteroides mobilizable insertion element, NBU1, integrates into the 3' end of a Leu-tRNA gene and has an integrase that is a member of the lambda integrase family. J Bacteriol. 178(12):3594-600.), P1 (Li Y, and Austin S. (2002) The P1 plasmid in action: time-lapse photomicroscopy reveals some unexpected aspects of plasmid partition. Plasmid. 48(3):174-8.), and T7 (Rezende, L. F., et al. (2002) Essential Amino Acid Residues in the Single-stranded DNA-binding Protein of Bacteriophage T7. Identification of the Dimer Interface. J. Biol. Chem. 277, 50643-50653.). Integrase maintains its activity when fused to other proteins.

Also disclosed are integrating enzymes of the disclosed compositions wherein the enzyme is a recombinase. For example, the recombinase can be a Cre recombinase, Flp recombinase, HIN recombinase, or any other recombinase. Recombinases are well-known in the art. An extensive list of recombinases can be found in Nunes-Duby S E, et al. (1998) Nuc. Acids Res. 26(2): 391-406, which is incorporated herein in its entirety for its teachings on recombinases and their sequences.

Also disclosed are integrating enzymes of the disclosed compositions wherein the enzyme is a retrotransposase. For example, the retrotransposase can be a GATE retrotransposase (Kogan G L, et al. (2003) The GATE retrotransposon in *Drosophila melanogaster*: mobility in heterochromatin and aspects of its expression in germ line tissues. Mol Genet Genomics. 269(2):234-42).

Other general techniques for integration into the host genome include, for example, systems designed to promote homologous recombination. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

Zinc Finger Nucleases

In another method, a zinc finger nuclease creates site-specific deletions via double-stranded DNA breaks that are repaired by non-homologous end joining (NHEJ). Zinc finger nucleases may also be used to create an insertion mutation by combining the ZFN with a homologously integrating cassette to create an insertion in the genomic DNA. Therefore, this genetic modification method can be used for both targeted (site-specific) DNA insertions and targeted DNA deletions. In one embodiment, the method involves transformation of a cell with a nucleic acid or mRNA construct minimally comprising DNA encoding a chimeric zinc finger nuclease (ZFN), which can be used to create a DNA deletion. In another embodiment, a second DNA construct can be provided that will serve as a template for repair of the cleavage site by homologous recombination. In this embodiment, a DNA insertion may be created. The DNA insertion may contain a gene trap cassette. In one embodiment, this method can be combined with spermatogonial stem cell technology or embryonic stem cell technology, as mentioned above. In another embodiment, this method can be combined with mobile DNA technology. This technique can also be done directly in the rat embryo.

Nucleic Acid Modification Methods

In one embodiment, a random mutation is created with a chemical mutagen and then a screen is performed for insertions in a particular cytokine gene. Chemical mutagens such as methane-sulfonic acid ethylester (EMS), N-ethyl-N-nitrosourea (ENU), diepoxyoctane and UV/trimethylpsorlalen may be employed to create nucleic acid sequence mutations.

Sequence editing methods can also be used that involve the delivery of small DNA fragments, hybrid DNA/RNA molecules, and modified DNA polymers to create sequence mismatches and nucleic acid mutations. RNA/DNA hybrids are molecules composed of a central stretch of DNA flanked by short RNA sequences that form hairpin structures. The RNA/DNA hybrids can produce single base-pair substitutions and deletions resulting in nucleotide mutations. Some other sequence editing examples include triplex forming oligonucleotides, small fragment homologous replacement, single stranded DNA oligonucleotides, and adeno-associated virus (AAV) vectors.

The invention also is directed to genetic expression modification or mutagenesis by delivery of a transgene that works in trans.

In one genetic modification method, RNA interference may be used to alter the expression of a gene. In another genetic modification method, the delivery of a transgene encoding a dominant negative protein may alter the expression of a target gene.

Vector Delivery Methods

The mutagenesis methods of this invention may be introduced into one or more cells using any of a variety of techniques known in the art such as, but not limited to, microinjection, combining the nucleic acid fragment with lipid vesicles, such as cationic lipid vesicles, particle bombardment, electroporation, DNA condensing reagents (e.g., calcium phosphate, polylysine or polyethyleneimine) or incorporating the nucleic acid fragment into a viral vector and contacting the viral vector with the cell. Where a viral vector is used, the viral vector can include any of a variety of viral vectors known in the art including viral vectors selected from the group consisting of a retroviral vector, an adenovirus vector or an adeno-associated viral vector.

DNA or other genetic material may be delivered through viral and non-viral vectors. These vectors can carry exogenous DNA that is used to genetically modify the genome of the rat. For example Adenovirus (AdV), Adeno-associated virus (AAV), and Retrovirus (RV) which contain LTR regions flanking a gene trap, transgene, cassette or interfering RNA are used to integrate and deliver the genetic material. Another delivery method involves non-viral vectors such as plasmids used for electroporation and cationic lipids used for lipofection. The non-viral vectors usually are engineered to have mechanisms for cell uptake, endosome escape, nuclear import, and expression. An example would be a non-viral vector containing a specific nuclear localization sequence and sequence homology for recombination in a targeted region of the genome.

There are a number of compositions and methods which can be used to deliver nucleic acids to cells, either in vitro or in vivo. For example, the nucleic acids can be delivered through a number of direct delivery systems such as, electroporation, lipofection, calcium phosphate precipitation, plasmids, cosmids, or via transfer of genetic material in cells or carriers such as cationic liposomes. Appropriate means for transfection, including chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed non-viral vectors for example, lipids such as liposomes, such as cationic liposomes (e.g., DOTMA, DOPE, DC-cholesterol) or anionic liposome, or polymersomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. Am. J. Resp. Cell. Mol. Biol. 1:95-100 (1989); Felgner et al. Proc. Natl. Acad. Sci USA 84:7413-7417 (1987); U.S. Pat. No. 4,897,355. Furthermore, the vector can be administered as a component of a microcapsule that can be targeted to specific cell types, such as macrophages, or where the diffusion of the compound or delivery of the compound from the microcapsule is designed for a specific rate or dosage.

In the methods described above, which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

These vectors may be targeted to a particular cell type via antibodies, receptors, or receptor ligands. The following references are examples of the use of this technology to target specific proteins to tumor tissue and are incorporated by reference herein (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129:57-80, (1992); and Roffler, et al., Biochem. Pharmacol, 42:2062-2065, (1991)). These techniques can be used for a variety of other specific cell types. Vehicles such as "stealth" and other antibody conjugated liposomes (including lipid-mediated drug targeting to colonic carcinoma), receptor-mediated targeting of DNA through cell specific ligands, lymphocyte-directed tumor targeting, and highly specific therapeutic retroviral targeting of murine glioma cells in vivo. The following references are examples of the use of this technology to target specific proteins to tumor tissue and are incorporated by reference herein (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis have been reviewed (Brown and Greene, DNA and Cell Biology 10:6, 399-409 (1991)).

Nucleic acids that are delivered to cells which are to be integrated into the host cell genome typically contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can be come integrated into the host genome.

Faslg Domains and Loss of Function Mutations

*Rattus norvegicus* Fas Ligand is a 278 amino acid (AA) protein. The protein consists of two module forms; the membrane form and soluble form. The membrane form is composed of AA 1-278, and the soluble form is composed of AA 127-278. The protein contains multiple protein domains. A cytoplasmic topological domain consists of AA 1-77; a extracellular topological domain consists of AA 100-278; a type II transmembrane protein single anchor domain consists of AA 78-99; a proline rich domain consists of AA 4-69; a poly-proline domain consists of AA 45-58. The *Rattus norvegicus* Fas Ligand protein contains one cleavage site at AA 126-127; glycosylation modification sites at AA 116. 247, 256; and disulfide bond connecting AA 199 and 230. The Faslg gene mRNA consists of 1417 base pairs with a coding sequence between base pairs 74-910.

Zhao et al. (Arch. Pharm. Res. 32(4), 575-581: 2009) Found that bp 305 through 370 are essential for Faslg mediated of apoptosis by activation of Caspases 8 and 9.

TABLE

Amino Acid changes resulting in cytokine-cytokine signaling pathway modification. This table displays some amino acid changes that are predicted to disrupt Faslg activity.

| Amino Acid | Faslg functional domain effected |
|---|---|
| 143-276 | Active Site |
| 145 | Trimer Interface |
| 185 | Trimer Interface |
| 189 | Trimer Interface |
| 241 | Trimer Interface |
| 246 | Trimer Interface |
| 272 | Trimer Interface |
| 276 | Trimer Interface |
| 160-161 | Receptor Binding Site |
| 166 | Receptor Binding Site |
| 205 | Receptor Binding Site |
| 212 | Receptor Binding Site |
| 217 | Receptor Binding Site |
| −281 | Promoter region |
| 1-77 | Cytoplasmic Domain |
| 78-99 | Signal Anchor |
| 100-278 | Extracellular Domain |
| 4-69 | Proline-Rich Region |

TABLE-continued

Amino Acid changes resulting in cytokine-cytokine signaling pathway modification. This table displays some amino acid changes that are predicted to disrupt Faslg activity.

| Amino Acid | Faslg functional domain effected |
|---|---|
| 45-58 | Poly-proline Region |
| 126-127 | Cleavage Site |
| 116 | Post-Translational Modification |
| 247 | Post-Translational Modification |
| 257 | Post-Translational Modification |
| 199-230 | Disulfide Bond |

Faslg Phenotypes

The Faslg gene encodes the protein Fas Ligand which is essential for cytokine mediated apoptosis of lymphocytes. Faslg plays a critical role in the regulation of leukocytes, B, T, and null lymphocytes, and neutrophils. All classes of immunoglobulin are regulated by Faslg. In the absence if functional Faslg antinuclear, dsDNA and thymocyte binding autoantibodies are spontaneously produced. Some Faslg mutations result in partial loss of function or "knockdown" and others result in full loss of function mutations or "knockout".

The Faslg activity resulting from a loss of function in one or several Faslg effectors has completely different and variable phenotypes; some resulting in less cytokine mediated immunodysregulation, autoimmune and inflammatory response. Complete loss of function or "knockout" of Faslg resulting in loss of function in all of its effectors always results in cytokine mediated dysregulation of cellular immunity, anti-nuclear and dsDNA autoantibody production and other forms of autoimmune response; resulting in severe and chronic inflammation in known animal models.

TABLE

Cytokine-Cytokine Signaling Mediated Autoimmune and Inflammatory Disease Phenotypes

| | Proliferation and Activity Effects | | | | Pro- | Immune | Primary | Homozygous |
|---|---|---|---|---|---|---|---|---|
| Gene | T | B | NK | M | Inflammatory | Response | Location | Phenotype |
| Faslg | + | + | N | N | T-cell hyperplasia (SLE) | Autoimmune hemolytic anemia (ALPS) Production of anti-nuclear and dsDNA autoantibody | Lymph Nodes | The inability to mediate cytotoxic T-cell death leads to uncontrolled lymphocyte proliferation resulting in multiple chronic inflammatory and autoimmune diseases. |
| Fas | + | + | N | N | Lymph node, spleen, liver hyperplasia | | Lymph Nodes Spleen | Lymphadenopathy & splenomegaly occurs, hepatocytes are resistant to Fas mediated apoptosis leading to an enlarged liver |
| INF-γ | + | + | − | − | Proliferative effects on T, B-cells, spleen enlargement | Cell mediated immunity is decreased | Spleen | Susceptibility to viral infection, and defective in |

TABLE-continued

| Cytokine-Cytokine Signaling Mediated Autoimmune and Inflammatory Disease Phenotypes | | | | | | | | |
|---|---|---|---|---|---|---|---|---|
| | Proliferation and Activity Effects | | | | Pro- | Immune | Primary | Homozygous |
| Gene | T | B | NK | M | Inflammatory | Response | Location | Phenotype |
| | | | | | | | | natural resistance, decreased production of macrophages and NK cells, deficient antigen-specific immunoglobulin response |
| TNFα | N | – | – | N | Decreased inflammation, reduced contact hyper-sensitivity | Cell mediated immunity is decreased, enhanced IgG responses | Thymus, Spleen | Susceptibility to viral infection, reduction in inflammatory responses, B-cell follicles are absent |
| IL-2 | – | N | – | + | Inability to suppress pro-inflammatory cytokines | Reduced polyclonal immune response, increased immunoglobulins | Lymph Nodes | Immuno-deficiency due to defective lymphokine |
| IL-10 | + | N | N | + | Mucosal hyperplasia, Chronic enterocolitis | 5-fold increase in IFN−γ producing T-cells | Spleen, Colon | Growth retardation, chronic inflammation of the bowels, extensive regenerative hyperplasia of mucosa leading to thickening of the intestinal wall |
| IL-12 | – | N | – | N | Hyper-sensitivity responses are reduced, | Defective IFN−γ and Th1 cytokine response, | Lymph Nodes | Cytokine mediated immunity is impaired, inflammatory responses are reduced |

CLUSTAL 2.0.10 multiple sequence alignment of rat and mouse Fas Ligand (Faslg) amino acid sequence. The sequence alignment shows close homology between the mouse and rat Faslg sequence; which has an alignment score of 90%. The homology of conserved domains and knowledge of insertion mutagenesis allows evidence that mutagenesis will create a total knockout rat Faslg.

```
rattus  ------------------------------------------------------------
Mus     TGAGGCTTCTCAGCTTCAGATGCAAGTGAGTGGGTGTCTCACAGAGAAGCAAAGAGAAGA  60

rattus  ------------------------------------------------------------
Mus     GAACAGGAGAAAGGTGTTTCCCTTGACTGCGGAAACTTTATAAAGAAAACTTAGCTTCTC 120

rattus  --------------TCAGAGTCCTGTCCTTGACACTTCAGTCTCC---ACAAGACTGAGA  43
Mus     TGGAGCAGTCAGCGTCAGAGTTCTGTCCTTGACACCTGAGTCTCCTCCACAAGGCTGTGA 180
                      ******* ************* * *******   ***** *** **
```

-continued

```
rattus GGAGGAAACCCTTTCCTGGGGCTGGGTGCCATGCAGCAGCCCGTGAATTACCCATGTCCC  103
Mus    GAAGGAAACCCTTTCCTGGGGCTGGGTGCCATGCAGCAGCCCATGAATTACCCATGTCCC  240
       * **************************************** *****************

rattus CAGATCTACTGGGTAGACAGCAGTGCCACTTCTCCTTGGGCTCCTCCAGGGTCAGTTTTT  163
Mus    CAGATCTTCTGGGTAGACAGCAGTGCCACTTCATCTTGGGCTCCTCCAGGGTCAGTTTTT  300
       ******* ************************  **************************

rattus TCTTGTCCATCCTCTGGGCCTAGAGGGCCAGGACAAAGGAGACCACCGCCTCCACCACCA  223
Mus    CCCTGTCCATCTTGTGGGCCTAGAGGGCCGGACCAAAGGAGACCGCCACCTCCACCACCA  360
        * ******** * *************** *  *********** ** ************

rattus CCTCCATCACCACTACCACCGCCTTCCCAACCACCCCCGCTGCCTCCACTAAGCCCTCTA  283
Mus    CCTGTGTCACCACTACCACCGCCATCACAACCACTCCCACTGCCGCCACTGACCCCTCTA  420
       ***   ***************** ** ******* *** ***** ***** * *******

rattus AAGAAGAAGGAC---AACATAGAGCTGTGGCTACCGGTGATATTTTTCATGGTGCTGGTG  340
Mus    AAGAAGAAGGACCACAACACAAATCTGTGGCTACCGGTGGTATTTTTCATGGTTCTGGTG  480
       ************   **** * * *************** ************* ******

rattus GCTCTGGTTGGAATGGGGTTAGGAATGTATCAACTCTTTCATCTACAGAAGGAACTGGCA  400
Mus    GCTCTGGTTGGAATGGGATTAGGAATGTATCAGCTCTTCCACCTGCAGAAGGAACTGGCA  540
       ***************** ************** ***** ** ** ***************

rattus GAACTCCGTGAGTTCACCAACCACAGCCTTAGAGTATCATCTTTTGAAAAGCAAATAGCC  460
Mus    GAACTCCGTGAGTTCACCAACCAAAGCCTTAAAGTATCATCTTTTGAAAAGCAAATAGCC  600
       *********************** ******* ****************************

rattus AACCCCAGCACACCCTCTGAAACCAAAAAGCCAAGGAGTGTGGCCCACTTAACAGGGAAC  520
Mus    AACCCCAGTACACCCTCTGAAAAAAAAGAGCCGAGGAGTGTGGCCCATTTAACAGGGAAC  660
       ******** *************  *** **** ************* ************

rattus CCCCGCTCAAGGTCCATCCCTCTGGAATGGGAAGACACATATGGAACTGCTTTGATCTCT  580
Mus    CCCCACTCAAGGTCCATCCCTCTGGAATGGGAAGACACATATGGAACCGCTCTGATCTCT  720
       **** ****************************************** *** ********

rattus GGAGTGAAGTATAAGAAAGGCGGCCTTGTGATCAATGAGGCTGGGTTGTACTTCGTATAT  640
Mus    GGAGTGAAGTATAAGAAAGGTGGCCTTGTGATCAACGAAACTGGGTTGTACTTCGTGTAT  780
       ******************** ************** **  **************** ***

rattus TCCAAAGTATACTTCCGGGGTCAGTCTTGCAACAGCCAGCCCCTAAGCCACAAGGTCTAT  700
Mus    TCCAAAGTATACTTCCGGGGTCAGTCTTGCAACAACCAGCCCCTAAACCACAAGGTCTAT  840
       ********************************** *********** *************

rattus ATGAGGAACTTTAAGTATCCTGGGGATCTGGTGCTAATGGAGGAGAAGAAGTTGAATTAC  760
Mus    ATGAGGAACTCTAAGTATCCTGAGGATCTGGTGCTAATGGAGGAGAAGAGGTTGAACTAC  900
       ********** *********** ************************** ****** ***

rattus TGCACTACTGGCCAGATATGGGCCCACAGCAGCTACCTAGGGGCAGTATTTAATCTTACC  820
Mus    TGCACTACTGGACAGATATGGGCCCACAGCAGCTACCTGGGGGCAGTATTCAATCTTACC  960
       *********** ************************** *********** *********

rattus GTTGCTGACCATTTATATGTCAACATATCTCAACTCTCTCTGATCAATTTTGAGGAATCT  880
Mus    AGTGCTGACCATTTATATGTCAACATATCTCAACTCTCTCTGATCAATTTTGAGGAATCT 1020
         **********************************************************

rattus AAGACCTTTTTTGGCTTATATAAGCTTTAAAGGAAAAAGCATTTTAGAATGATCTATTAT  940
Mus    AAGACCTTTTTCGGCTTGTATAAGCTTTAAAAGAAAAAGCATTTTAAAATGATCTACTAT 1080
       *********** ***** ************* ************** ********* ***

rattus TCTTTATCATGGATGCCAGGAATATTGTCTTCAATGAGAGTCTTCTTAAGACCAATTGAG 1000
Mus    TCTTTATCATGGGCACCAGGAATATTGTCTTGAATGAGAGTCTTCTTAAGACCTATTGAG 1140
       ************   **************** ********************* ******

rattus --------------------CCACAAAGACC--------ACAAGGTCCAACAGGTCAGCT 1032
Mus    ATTAATTAAGACTACATGAGCCACAAAGACCTCATGACCGCAAGGTCCAACAGGTCAGCT 1200
                           ***********         ********************

rattus ACCCTTCATTTTCTAGAGGTCCATGGAGTGGTCCTTAATGCCTGCATCATGAGCCAGATG 1092
Mus    ATCCTTCATTTTCTCGAGGTCCATGGAGTGGTCCTTAATGCCTGCATCATGAGCCAGATG 1260
       * ************ *********************************************

rattus GGAAGAAGACTGTTCCTGAGGAACATAAAGTTTTGGGCTGCTGTGTGGCAATGCAGAGGC 1152
Mus    GAAGGAGGTCTGTGACTGAGGGACATAAAGCTTTGGGCTGCTGTGTGACAATGCAGAGGC 1320
       * * ** * ****  ****** ******** **************** ************

rattus AAAGAGAAGGAACTGTCTGATGTTAAATGGCCAAGAGCATTTTAGCCATTGAAGAAAAAA 1212
Mus    ACAGAGAAAGAACTGTCTGATGTTAAATGGCCAAGAGAATTTTAACCATTGAAGAAGACA 1380
       * ****** **************************** ****** *********** * *
```

-continued

```
rattus AAAACCTTTAAACTCACCTTCCAGGGTGGGTCTACTTGCTACCTCACAGGAGGCCGTCTT 1272
Mus    ----CCTTTACACTCAC-TTCCAGGGTGGGTCTACTTACTACCTCACAG-AGGCCGTTTT 1434
           ****** ****** ******************* *********** ******* **

Rattus TTAGACACATGGTTGTGGTATGACTATACAAGGGTGAGAAAGGATGCTAGGTTTCATGGA 1332
Mus    TGAGACA--TAGTTGTGGTATGAATATACAAGGGTGAGAAAGGAGGCTCA-TTTGACTGA 1491
       * *****  * ************ ******************** ***   *** *  **

Rattus TAAGCTAGAGACTGAAAAAA-GCCAGTGTCCCATTGGCATCATCTTTATTTTTAACTGAT 1391
Mus    TAAGCTAGAGACTGAAAAAAAGACAGTGTCTCATTGGCACCATCTTTACTGTTACCTAAT 1551
       ******************** * ******* ******** ******** * *** ** **

Rattus GTTTTCTGAGCCCACCTTTGATGCTAACAGAGAAATAAGAGGGGTGTTTGAGGCACAAGT 1451
Mus    GTTTTCTGAGCCGACCTTTGATCCTAACGGAGAAGTAAGAGGGATGTTTGAGGCACAAAT 1611
       ************ ********* ***** ***** ******** ************** *

Rattus CATTCTCTACATAGCATGTGTACCTCCAGTGCAATGATGTCTGTGTGTGTTTTTATGTAT 1511
Mus    CATTCTCTACATAGCATGCATACCTCCAGTGCAATGATGTCTGTGTGT--TTGTATGTAT 1669
       ******************  ****************************  ** *******

rattus GAGAGTAGAGCGATTCTAAAGAGTCACATGAGTACAACGCGTACATTACGGAGTACATAT 1571
Mus    GAGAGCAAACAGATTCTAAGGAGTCATATAAATAAAATATGTACATTATGGAGTACATAT 1729
       ***** * *  ******** ****** ** * ** **   ******** ***********

rattus TAGAAACGTATGTGTTACATTTGATGCTAGAATATCTGAATGTTTCTTGCTA-------- 1623
Mus    TAGAAACCT----GTTACATTTGATGCTAGA-TATCTGAATGTTTCTTGGCAATAAACTC 1784
       ******* *    ****************** *****************  *

rattus ------------------------------------------------------------
Mus    TAATAGTCTTCAAAATCTTTTATTATCAGCTACTGATGCTGTTTTTCTTTAATACAACTA 1844

rattus ------------------------------------------------------------
Mus    GTATTTATGCTCTGAACATCCTAATGAGGAAAAGACAAATAAAATTATGTTATAGAATAC 1904

rattus ---------------------------------
Mus    AGAAATGCCTTAAGGACATAGACTTTGGAAATC                            1937
```

Cytokine-Cytokine Signaling Knockout Phenotypes.

Fas Ligand (Faslg−/−) Knockout, Complete Loss of Function Phenotypes

Nagata et al. (Nat Genetics 95', 11) created Faslg−/− KO mice by homologous recombination with a targeting vector which disrupted most of the ninth exon. The 9th exon contains the cytoplasmic essential region of the FASLG protein, and its disruption results in a completely null allele. The lymph nodes and spleen of Faslg KO mice were enlarged. At the age of 47 weeks the lymph nodes of Faslg−/− KO mice were up to 96-fold larger than WT mice, and the spleen was 7.5-fold larger. Other organs such as the thymus, kidney, liver, salivary gland, and pancreas were all of normal size; although dispositions of immune complexes were found in the glomeruli of the kidney. The number of lymphocytes and neutrophils found in the enlarged organs were at least 4-fold more than WT mice. Spontaneous inflammatory disease of the lung occurred in Faslg−/− KO mice as massive amounts of lymphocytes and macrophages accumulated in the alveolar space. When the total serum protein level was measured in Faslg deficient mice it was found to be similar to WT levels. However, total leukocyte and circulating lymphocytes rose well over 3-fold the amount found in WT mice, and closely correlated with the increase in lymph node size. By the age of 24 weeks there was a significant increase in all three lymphoid sets; B-, T-, and Thy-1(−) cells rose to 33-fold the amount found in WT mice. All the classes of immunoglobulin were elevated in Faslg−/− KO mice when compared to WT by the age of 20 weeks. When immunoglobulin isotypes were measured in Faslg deficient mice 9 of 10 clinically affected mice showed a significant increase in at least two isotypes. Auto-antibodies directed against nuclear antigens were detected in all Faslg−/− KO mice by the age of 16 weeks. The serum of Faslg deficient mice also had severely elevated levels of anti-dsDNA autoantibodies which met or exceeded other murine models of autoimmune disease and human autoimmune disease levels. Auto-antibodies were bound to over 50% of target thymocytes in Faslg−/− mice compared to the 7% bound in WT mice. These data, along with the presence of massive early onset of lymphoid hyperplasia with hyperimmunoglobulinemia and production of autoantibodies against native DNA indicate that the Fas Ligand (Faslg−/−) KO deficiency occurs by disrupting cytokine-cytokine signaling and is an autoimmune and chronic inflammation phenotype.

Fas (TNF Receptor Superfamily, Member 6) −/− KO Phenotype.

Nagata et al. (Nature Genetics V11, 1995) disrupted the Fas cytokine signaling allele by homologous recombination using a targeting vector. The vector was inserted into exon 9 disrupting the essential cytoplasmic region of Fas which mediates apoptosis. The Fas−/− KO mice show lymphadenopathy and splenomegaly within the first 8 weeks of life. The lymph nodes and spleen of the Fas deficient mice are enlarged continuously, and by the age of 16 weeks are found to be up to 40-fold larger than WT mice. The cells that accumulate in these organs which contribute to the lymph node and spleen extensive size are T lymphocytes bearing the atypical phenotype of Thy1+ B220+ CD4− CD8−. Lymphocytosis along with the sporadic infiltration of lymphocytes into other organs such as the lungs and liver occurred, but was not accompanied by hyperplasia of the thymus. In WT cells and mice stimulation of Fas with anti-Fas antibody results in apoptosis of thymocytes. When thymocytes from Fas−/− KO mice were treated with anti-Fas antibody no thymocytes were killed. Whereas in Fas WT mice over 60% of thymocytes were killed within 16 hours of treatment with anti-Fas. The liver of Fas−/− KO mice was found to be up to 60% heavier at 16 weeks of age when compared to WT mice. When the enlarged liver was analyzed it was found that the nuclear size and the number of the hepatocytes was far greater than in WT mice livers; although hepatocyte function was not altered. Hepatocytes from Fas−/− mice were resistant to Fas-mediated apoptosis. Less than 5% of hepatocytes died in the presence of anti-Fas antibody compared to the 90% death rate in WT mice. The Fas−/− KO mice exhibit massive lymphoproliferation and hyperplasia of the liver. The phenotype is attributed to a disruption in cytokine-cytokine signaling. The lymphocytes that accumulate in organs produce cytokines which stimulate hepatocyte growth in the liver. The Fas−/− KO mice exhibit a cytokine-cytokine signaling mediated immune dysregulation phenotype.

Interferon-γ (IFN-γ) Knockout Complete Loss of Function Phenotype.

Stewart et al (Science 259, 195) introduced a targeting vector into exon 2 of the IFN-γ gene in mice. The vector contains a termination codon at amino acid position 30 in the gene and rendered it completely null. In wild-type mice that are infected with a pathogen such as *Mycobacterium bovis* macrophage activation occurs at a high level with enhanced MHC class II and ability to kill the microorganisms. When INF-γ deficient mice are infected with pathogens macrophage activation is severely reduced along with the expression of antimicrobial products. The cytokine-cytokine cell-mediated immunity is altered in INF-γ KO mice. Sub-lethal doses of infectious microbes resulted in up to 100-fold more colony forming units (CFU) in the lung, liver, and spleen and increased the mortality rate of the cytokine signaling deficient mice. When T-cell function and proliferation was measured in INF-γ−/− KO spleen cells they showed an enhanced proliferation, forming dense overgrown layers in vitro. Cytolytic activity and proliferation of cytotoxic T cells (CTL's) was measured by cultured irradiated allogenic stimulator cells. Cytolytic activity was found to be much greater in INF-γ−/− KO mice compared to WT effectors. INF-γ−/− KO mice were found to have a much lower resting splenic NK activity. These data indicate that the INF-γ−/− KO is a model for both infectious and autoimmune disease and its role as an immunoregulatory cytokine is crucial for proper cytokine-cytokine signaling.

TNF-α Knockout, Complete Loss of Function Phenotype.

Kollias et al. (*J. Exp. Med.* 1996, 184: 1397-1411) described the procedures and phenotypes of a TNF-α−/− KO mouse model for cytokine-cytokine mediated inflammation and autoimmune responses. A targeting vector containing 40 bp of the TNF-α 5' UTR was inserted into the mouse TNF-α gene. The vector replaced the translation initiation codon, the entire first exon and a portion of the first intron. The insertion rendered the gene completely null. Contact sensitivity (CH) was studied in TNF-α KO mice by contact allergen oxazolone. First the mice were sensitized by application of oxazolone on abdominal skin. Oxazolone was then painted on one ear of TNF-α KO mice and on one ear of WT mice. When inflammation of the two mice was compared a significant decrease in hypersensitive response was recorded in TNF-α KO. The TNF-α deficient mice showed a 33% decrease in ear swelling when compared to WT; indicating that TNF-α plays an enhancing role in contact hypersensitivity. When the spleen of non-immunized TNF-α KO mice was immune-stained with antibodies the absence of primary B cell follicles was revealed. When stained with a marker for follicle dendritic cells (FDC) it was found that TNF-α KO mice lacked FDC networks. When immunocytochemical staining of spleen sections of TNF-α KO mice completely lacked FDCs and typical germinal centers. NK cell-derived TNF-α cytokines are implicated in immune responses to TI antigens. The ability of TNF-α KO mice to produce antibodies in response to T1 antigens was measured by immunization by type 1 & 2 TI antigen. Anti-TNP IgG responses were slightly decreased in TNF-α KO mice. TNF-α KO also exhibited enhanced IgG responses to type 2 TI antigen. The TNF-α KO mice demonstrated the importance of the gene in LPS-mediated toxicity, and regulating of primary B-cells, FDC networks and germinal centers. The mouse model was essential in validating the inhibition of TNF-α as a treatment for chronic inflammatory and autoimmune diseases in human patients.

Interleukin-2 (IL-2)−/− Knockout, Complete Loss of Function Phenotype.

Horak et al. (*Nature* 1991, 352: 621-623) described the introduction of a neomycin resistance containing targeting vector into the third exon of the IL-2 locus in mouse. The vector introduced multiple stop codons and rendered the allele completely null. Observance via flow cytometry of thymocyte subtypes displayed no difference in thymocyte composition or cell numbers in the thymus between knockout and control mice. Cytokine deficiency was revealed on the functional level, however. Cells from the thymus, lymph node, and spleen of IL-2 KO mice demonstrated inferior response to polyclonal T-cell activators when compared to WT. When the ability for primed B-cells to secrete immunoglobulin was studied drastic differences were revealed in IL-2 KO mice and WT. Serum concentration of IgG1 was 1,600-2,700 μg/mL in IL-2 KO mice and <50-60 μg/mL in WT mice. Carding et al. (*Cellular Immunology* 187, 52-66, 1998) measured cytokine production in IL-2 KO mice as the colitis disease model progressed. The group found that a large accumulation of cytokine producing CD4+ and CD8+ T cells occurred. As the disease progresses increases in IL-4, INF-γ, and TNF-α producing CD4+ cells occurred. Many of these cells were found to overproduce more than one cytokine. The phenotype of the IL-2 KO mouse model for chronic inflammatory and autoimmune disease was characterized to be attributed to a disruption in cytokine-cytokine signaling. The overproduction or dysregulation of cytokine interactions is clearly displayed in the autoimmune and chronic inflammatory phenotype of this model.

Interleukin-12 (IL-12)−/− KO, Total Loss of Function Phenotype.

Gately et al. (*Immunity* 1996, 4: 471) created a mouse with a null mutation in the IL-12 gene. A replacement vector was inserted into exon 3 replacing a portion of the coding region and rendering the locus completely null. The lytic activity of NK-cells was tested by five different assays in WT versus IL-12 KO mice. The NK lytic activity of IL-12−/− mice was found to be 66% of the mean lytic activity in WT mice. IL-12 KO mouse response to endotoxin lipopolysaccharide (LPS) was examined by administration of LPS to IL-12 deficient mice and control mice, and serum levels of IFN-γ were measured. The LPS induced INF-γ serum levels of IL-12−/− mice were significantly reduced to 17% of that found in WT mice. Antigen induced cytokine production is a major indicator in of cytokine-cytokine signaling defects; therefore, IL-12 KO and WT mice were immunized and compared for cytokine production and T cell proliferation. By observance of draining lymph nodes immunized IL-12−/− mice showed a major deficiency in the ability to secrete INF-γ and in contrast had an increase in antigen induced IL-4 production. Since the production of type 1 cytokines is essential for cytokine-cytokine signaling and cell-mediated immunity, CTL and delayed hyper-sensitivity (DH) responses were studied in the IL-12−/− mice. The IL-12 deficient mice were found to produce normal CTL responses were immunized with allogenic splenocytes in the footpad and when draining lymph nodes were harvested. The normal CTL responses of IL-12−/− mice were contradicted by their deficiency in generating DH reaction. When IL-12−/− and WT mice were immunized by methylated bovine serum albumin (MBSA) and DH reactions were measured, foot swelling was inhibited by 47% in IL-12 KO mice. The lack of inflammatory response indicates an immune cell inflammatory response defect which is mediated by cytokine-cytokine signaling.

Interleukin-10 (IL-10)−/− KO, Complete Loss of Function Phenotype.

Muller et al. (*Cell* 1993, 75: 263-274) studied the in vivo functions of cytokine IL-10 by creating a mouse mutant for that allele. A 500 bp fragment containing codons 5-55 from IL-10, a termination codon, and a neo cassette was introduced into codon 3 of the mouse IL-10 gene, rendering it completely null. Levels of IL-4, 5, & 10 are dramatically increased in spleens of WT mice when stimulated with mitogen concanavalin A (ConA). However, when measured by enzyme linked immunosorbent assay (ELISA) IL-10−/− mice only display production of IL-5. Infection of mice with nematode *N. brasiliensis* provokes Th2 response with the increased production of IL-4, 5, & 10. When IL-10−/− KO mice were infected the levels of splenic IFN-γ were 5-fold that of spleens in WT mice When measured via immunostaining and flow cytometry a 3-fold increase in IFN-γ producing T-cells was found in IL-10 deficient mice. Therefore, a cytokine-cytokine signaling, cell-mediated immune response is induced in IL-10−/−. This immune response is normal suppressed by WT IL-10 in control mice. The phenotype illustrates the IL-10 gene as essential for proper cytokine-cytokine signaling, and plays a major role in immune response to pathogens.

EXAMPLES

The rat and progenies thereof of the present invention may be any rat or progenies thereof, so long as they are a rat or progenies thereof in which genome is modified so as to have decreased or deleted activity of the cytokine-cytokine signaling pathway gene.

Gene Disruption Technique which Targets at a Gene Encoding Fas Ligand (Faslg)

The gene disruption method may be any method, so long as it can disrupt the gene of the target enzyme. Examples include a homologous recombination method, a method using retrovirus, a method using DNA transposon, and the like.

(a) Preparation of the Rat and Progenies Thereof of the Present Invention by Homologous Recombination The rat and the progenies thereof of the present invention can be produced by modifying a target gene on chromosome through a homologous recombination technique which targets at a gene encoding the cytokine-cytokine signaling pathway gene. The target gene on chromosome can be modified by using a method described in Gene Targeting, A Practical Approach, IRL Press at Oxford University Press (1993) (hereinafter referred to as "Gene Targeting, A Practical Approach"); or the like, for example.

Based on the nucleotide sequence of the genomic DNA, a target vector is prepared for homologous recombination of a target gene to be modified (e.g., structural gene of the cytokine-cytokine signaling pathway gene, or a promoter gene). The prepared target vector is introduced into an embryonic stem cell and a cell in which homologous recombination occurred between the target gene and target vector is selected.

The selected embryonic stem cell is introduced into a fertilized egg according to a known injection chimera method or aggregation chimera method, and the embryonic stem cell-introduced fertilized egg is transplanted into an oviduct or uterus of a pseudopregnant female rat to thereby select germ line chimeras.

The selected germ line chimeras are crossed, and individuals having a chromosome into which the introduced target vector is integrated by homologous recombination with a gene region on the genome which encodes the cytokine-cytokine signaling pathway protein are selected from the born offspring.

The selected individuals are crossed, and homozygotes having a chromosome into which the introduced target vector is integrated by homologous recombination with a gene region on the genome which encodes the cytokine-cytokine signaling pathway protein in both homologous chromosomes are selected from the born offspring. The obtained homozygotes are crossed to obtain offspring to thereby prepare the rat and progenies thereof of the present invention.

(b) Preparation of the Rat and Progenies Thereof of the Present Invention by a Method Using a Transposon The rat and progenies thereof of the present invention can be prepared by using a transposon system similar to that described in Nature Genet., 25, 35 (2000) or the like, and then by selecting a mutant of the cytokine-cytokine signaling pathway gene.

The transposon system is a system in which a mutation is induced by randomly inserting an exogenous gene into chromosome, wherein an gene trap cassette or exogenous gene interposed between transposons is generally used as a vector for inducing a mutation, and a transposase expression vector for randomly inserting the gene into chromosome is introduced into the cell at the same time. Any transposase can be used, so long as it is suitable for the sequence of the transposon to be used. As the gene trap cassette or exogenous gene, any gene can be used, so long as it can induce a mutation in the DNA of the cell.

The rat and progenies thereof of the present invention can be prepared by introducing a mutation into a gene encoding the cytokine-cytokine signaling pathway associated protein, and then by selecting a rat of interest in which the DNA is mutated.

Specifically, the method includes a method in which a rat of interest in which the mutation occurred in the gene encoding the Ada protein is selected from mutants born from generative cells which are subjected to mutation-inducing treatment or spontaneously generated mutants. In another embodiment, the cytokine-cytokine signaling pathway gene is one of several known cytokine-cytokine signaling pathway genes, such as (Fas, IFNγ, TNF-α, IL-2, IL-10, IL-12, Cxcr2(Il8rb), Ccr4, Ccr9, Cx3cr1, and Vegf). The generative cell includes cells capable of forming an individual such as a sperm, an ovum or a pluripotent cells. The generative cell may also be a somatic cell and the animal may then be created by somatic cell nuclear transfer.

Examples in which several methods described above have been employed by the inventors to create a cytokine-cytokine signaling pathway model phenotype in *Rattus norvegicus* are described below.

Genetic modification to *Rattus norvegicus* cytokine-cytokine signaling pathway gene Fas Ligand (Faslg) was carried out by a DNA transposon insertional mutagenesis method similar to that described in Nature Genet., 25, 35 (2000). The DNA transposon-mediated genetically modified allele was designated FaslgTn(sb-T2/Bart3)2.237Mcwi. The mutant strain symbol for the rat was designated F344-FaslgTn(sbT2/Bart3)2.237Mcwi.

The DNA transposon insertion occurred in chromosome 13, within intron 1 of the rat Faslg gene. The sequence tag map position was between base pairs: 77473736-77473776. The sequence tag was: TATAAATGGTCAGCAACGGTAA-GATTAAATACTGCCCCTAG. Thus, a DNA transposon was inserted into the Faslg gene of *Rattus norvegicus* rendering the gene completely inactive. Fas Ligand (Faslg −/−) KO rats are unable to mediate lymphocyte apoptosis leading to uncontrolled proliferation of B-, T- and null-cell lymphocytes. All classes of immunoglobulins production is increased at least three fold. All lymph nodes and spleens were enlarged in Faslg−/− rats. All Faslg−/− rats exhibited extensive lung inflammatory disease. Significant immune complexes were found to deposit in the glomeruli of Faslg−/− rats. Anti-nuclear, dsDNA, and thymocyte binding autoantibodies are produced in high numbers in all Faslg−/− rats. The phenotype was that of cytokine-cytokine signaling mediated immune dysregulation resulting in chronic inflammation and severe autoimmune response rat.

The practice of the present invention will employ, unless otherwise indicated, conventional techniques of molecular biology (including recombinant techniques), microbiology, cell biology and biochemistry, which are within the skill of the art.

The invention claimed is:

1. A genetically modified rat or progeny of the rat, wherein the rat or its progeny comprise in at least some of its cells a genome comprising a disruption of one or more cytokine genes that results in the misexpression of the one or more cytokine genes, wherein the rat or its progeny exhibits a greater susceptibility to a cytokine-mediated autoimmune and/or inflammatory disease than a rat or progeny rat not comprising the genetic mutation.

2. The genetically modified rat of claim 1, wherein the one or more cytokine genes are conditionally misexpressed.

3. The rat of claim 2, wherein the misexpression results in decreased expression of one or more cytokine genes.

4. The genetically modified rat of claim 1, wherein the cytokine gene is selected from the group consisting of Faslg, Fas, IFN-γ, TNF-α, IL-2, IL-10, IL-12, Cxcr2(118rb), Ccr4, Ccr9, Cx3crl, Vegf, Prkdc and Ada.

5. The genetically modified rat of claim 1, wherein the cytokine gene is selected from the group consisting of Faslg and Fas.

6. The genetically modified rat of claim 1, wherein the cells are somatic cells.

7. The genetically modified rat of claim 6, wherein the cells are hepatocytes.

8. The genetically modified rat of claim 1, wherein the cytokine gene is disrupted by removal of DNA encoding all or part of the cytokine protein, transposon insertion mutation, insertion mutation, deletion mutation, or introduction of a cassette or gene trap by recombination.

9. The genetically modified rat of claim 1, wherein the rat is homozygous for the one or more disrupted genes or loci.

10. The genetically modified rat of claim 1, wherein the rat is heterozygous for the one or more disrupted genes or loci.

11. A genetically modified rat or progeny of the rat, wherein the rat or its progeny comprise in at least some of its cells a genome comprising a disruption of one or more cytokine genes that results in the rat or its progeny exhibiting a greater susceptibility to a cytokine-mediated autoimmune and/or inflammatory disease than a rat or progeny rat not comprising the genetic mutation.

12. The genetically modified rat of claim 11, wherein the disruption causes a complete loss-of-function phenotype.

13. The genetically modified rat of claim 11, wherein the disruption causes a partial loss-of-function phenotype.

14. The genetically modified rat of claim 11, wherein the disruption causes a phenotype selected from the group consisting of lymphocyte proliferation, macrophage and immunoglobulin dysfunction, native DNA autoantibody production, contact sensitivity deficiency, and chronic inflammation.

15. The genetically modified rat of claim 11, wherein the protein product of the cytokine gene is associated with a phenotype that is characterized as cytokine-mediated autoimmune and/or inflammatory disease.

16. The genetically modified rat of claim 11, wherein the cytokine gene is selected from the group consisting of Faslg, Fas, IFN-γ, TNF-α, IL-2, IL-10, IL-12, Cxcr2(118rb), Ccr4, Ccr9, Cx3crl, Vegf, Prkdc and Ada.

17. The genetically modified rat of claim 11, wherein the cytokine gene is selected from the group consisting of Faslg and Fas.

18. The genetically modified rat of claim 11, wherein the one or more cytokine genes or loci are disrupted by transposon insertion mutations.

19. The genetically modified rat of claim 11, wherein the one or more cytokine genes or loci are disrupted by deletion mutation.

20. The genetically modified rat of claim 11, wherein the one or more cytokine genes or loci are disrupted by the introduction of a cassette or gene trap by recombination.

21. The genetically modified rat of claim 11, wherein the rat is homozygous for the one or more disrupted genes or loci.

22. The genetically modified rat of claim 11, wherein the rat is heterozygous for the one or more disrupted genes or loci.

23. The genetically modified rat of claim 11, wherein the phenotype results from a diminished amount, relative to the wild-type phenotype, of a protein selected from the group consisting of Faslg and Fas.

24. A method for determining whether a compound is potentially useful for treating or alleviating the symptoms of a cytokine gene disorder comprising (a) providing an isolated genetically modified rat cell comprising a genome comprising a disruption of one or more cytokine genes that causes the one or more cytokine genes to be misexpressed, wherein the rat exhibits a greater susceptibility to a cytokine-mediated autoimmune and/or inflammatory disease than a rat not comprising the genetic mutation, (b) contacting the cell with a compound, and (c) monitoring the activity of the cytokine protein, such that a change in activity in response to the compound indicates that the compound is potentially useful for treating or alleviating the symptoms of a cytokine gene disorder.

25. The method of claim 24, wherein the method is used for testing for activity of a candidate cytokine modulating agent.

26. A screening method for identifying useful compounds, comprising (a) providing an assay system comprising a rat model system comprising a genetically modified rat or progeny of the rat, wherein the rat or its progeny comprise in at least some of its cells a genome comprising a disruption of one or more cytokine genes that results in the misexpression of the one or more cytokine genes, wherein the rat or its progeny exhibits a greater susceptibility to a cytokine-mediated autoimmune and/or inflammatory disease than a rat or progeny rat not comprising the genetic mutation;

(b) contacting the model system with a candidate test agent; and (c) detecting a phenotypic change in the model system that indicates that the cytokine function is restored when compared relative to wild-type cells.

27. The screening method of claim 26, wherein the method is used for testing for activity of a candidate cytokine modulating agent.

28. The screening method of claim 26, wherein the candidate cytokine modulating agent modulates T-lymphocyte-mediated apoptosis or native DNA autoantibody production.

29. The screening method of claim 26, wherein the cytokine modulating agent causes altered cytokine gene expression that results in a detectable phenotype.

30. The screening method of claim 26, wherein the phenotype is selected from the group consisting of altered levels of T-, B-, and Natural Killer (NK)-cells, impaired macrophage and immunoglobulin function, and increases in susceptibility to autoimmune diseases, as compared to control animals having normal cytokine gene expression.

31. The screening method of claim 26, wherein the method is used for identifying useful compounds for the treatment of a disease or condition selected from the group consisting of autoimmune and inflammatory disease.

32. The screening method of claim 26, wherein the method is used for immunological studies, toxicology studies, and infectious disease studies.

33. The screening method of claim 30, wherein the cytokine gene is selected from the group consisting of Faslg, Fas, IFN-γ, TNF-α, IL-2, IL-10, IL-12, Cxcr2(118rb), Ccr4, Ccr9, Cx3crl, Vegf, Prkdc and Ada.

34. The screening method of claim 30, wherein the cytokine gene is selected from the group consisting of Faslg and Fas.

35. The screening method of claim 30, wherein the one or more cytokine genes or loci are disrupted by removal of DNA encoding all or part of the cytokine protein.

36. The screening method of claim 30, wherein the one or more cytokine genes or loci are disrupted by transposon insertion mutations.

37. The screening method of claim 30, wherein the one or more cytokine genes or loci are disrupted by deletion mutation.

38. The screening method of claim 30, wherein the one or more cytokine genes or loci are disrupted by the introduction of a cassette or gene trap by recombination.

39. A screening method for identifying useful compounds, comprising (a) providing an assay system comprising a model system comprising a genetically modified rat at least some of whose cells comprise a genome comprising a disruption of one or more cytokine genes that causes the one or more cytokine genes to be misexpressed, wherein the rat exhibits a greater susceptibility to a cytokine-mediated autoimmune and/or inflammatory disease than a rat not comprising the genetic mutation;

(b) contacting the model system with a candidate test agent; and (c) detecting a change in cytokine polypeptide expression or activity between the presence and absence of the candidate test agent that indicates the presence of a candidate modulating agent.

40. The screening method of claim 39, wherein the candidate cytokine modulating agent causes altered cytokine gene expression that results in a detectable phenotype.

41. The screening method of claim 39, wherein the phenotype is selected from the group consisting of altered levels of T-, B-, and natural Killer (NK)-cells, impaired macrophage and immunoglobulin function, and increases in susceptibility to autoimmune diseases, as compared to control animals having normal cytokine gene expression.

42. The screening method of claim 39, wherein the method is used for identifying useful compounds for the treatment of a disease or condition selected from the group consisting of autoimmune and inflammatory disease.

43. The screening method of claim 39, wherein the method is used for immunological studies, toxicology studies, and infectious disease studies.

44. The screening method of claim 40, wherein the cytokine gene is selected from the group consisting of Faslg, Fas, IFN-γ, TNF-α, IL-2, IL-10, IL-12, Cxcr2(118rb), Ccr4, Ccr9, Cx3crl, Vegf, Prkdc and Ada.

45. The screening method of claim 40, wherein the cytokine gene is selected from the group consisting of Faslg and Fas.

46. The screening method of claim 26, wherein the one or more cytokine genes are selected from Faslg, Fas, IFN-γ, TNF-α, IL-2, Prkdc, IL-10, IL-12α and Ada.

47. The method of claim 24, wherein the candidate cytokine modulating agent modulates T-lymphocyte-mediated apoptosis or native DNA autoantibody production.

* * * * *

UNITED STATES PATENT AND TRADEMARK OFFICE

CERTIFICATE OF CORRECTION

PATENT NO. : 8,558,055 B2
APPLICATION NO. : 12/842418
DATED : October 15, 2013
INVENTOR(S) : Eric M. Ostertag et al.

It is certified that error appears in the above-identified patent and that said Letters Patent is hereby corrected as shown below:

In the Claims

Please correct the claims as follows:

Claim 4, Column 53, line 61, delete "(118rb)" and add -- (IL8RB) --
Claim 16, Column 55, line 12, delete "(118rb)" and add -- (IL8RB) --
Claim 33, Column 56, line 26, delete "(118rb)" and add -- (IL8RB) --
Claim 44, Column 57, line 10, delete "(118rb)" and add -- (IL8RB) --

Signed and Sealed this
Thirty-first Day of December, 2013

Margaret A. Focarino
*Commissioner for Patents of the United States Patent and Trademark Office*

SEQUENCE LISTING

```
<160> NUMBER OF SEQ ID NOS: 9

<210> SEQ ID NO 1
<211> LENGTH: 1622
<212> TYPE: DNA
<213> ORGANISM: Rattus norvegicus

<400> SEQUENCE: 1

tcagagtcct gtccttgaca cttcagtctc cacaagactg agaggaggaa accctttcct     60

ggggctgggt gccatgcagc agcccgtgaa ttacccatgt ccccagatct actgggtaga    120

cagcagtgcc acttctcctt gggctcctcc agggtcagtt ttttcttgtc catcctctgg    180

gcctagaggg ccaggacaaa ggagaccacc gcctccacca cccctccatc accactacca    240

ccgccttccc aaccaccccc gctgcctcca ctaagccctc taaagaagaa ggacaacata    300

gagctgtggc taccggtgat atttttcatg gtgctggtgg ctctggttgg aatggggtta    360

ggaatgtatc aactctttca tctacagaag gaactggcag aactccgtga gttcaccaac    420

cacagcctta gagtatcatc ttttgaaaag caaatagcca accccagcac accctctgaa    480

accaaaaagc caaggagtgt ggcccactta acagggaacc cccgctcaag gtccatccct    540

ctggaatggg aagacacata tggaactgct ttgatctctg gagtgaagta taagaaaggc    600

ggccttgtga tcaatgaggc tgggttgtac ttcgtatatt ccaaagtata cttccggggt    660

cagtcttgca acagccagcc cctaagccac aaggtctata tgaggaactt taagtatcct    720

ggggatctgg tgctaatgga ggagaagaag ttgaattact gcactactgg ccagatatgg    780

gcccacagca gctacctagg ggcagtattt aatcttaccg ttgctgacca tttatatgtc    840

aacatatctc aactctctct gatcaatttt gaggaatcta agaccttttt tggcttatat    900

aagctttaaa ggaaaaagca ttttagaatg atctattatt ctttatcatg gatgccagga    960

atattgtctt caatgagagt cttcttaaga ccaattgagc cacaaagacc acaaggtcca   1020

acaggtcagc tacccttcat tttctagagg tccatggagt ggtccttaat gcctgcatca   1080

tgagccagat gggaagaaga ctgttcctga ggaacataaa gttttgggct gctgtgtggc   1140

aatgcagagg caaagagaag gaactgtctg atgttaaatg gccaagagca ttttagccat   1200

tgaagaaaaa aaaaaccttt aaactcacct tccagggtgg gtctacttgc tacctcactg   1260

gaggccgtct tttagacaca tggttgtggt atgactatac aagggtgaga aaggatgcta   1320

ggtttcatgg ataagctaga gactgaaaaa agccagtgtc ccattggcat catctttatt   1380

tttaactgat gttttctgag cccacctttg atgctaacag agaaataaga ggggtgtttg   1440

aggcacaagt cattctctac atagcatgtg tacctccagt gcaatgatgt ctgtgtgtgt   1500

ttttatgtat gagagtagag cgattctaaa gagtcacatg agtacaacgc gtacattacg   1560

gagtacatat tagaaacgta tgtgttacat ttgatgctag aatatctgaa tgtttcttgc   1620
```

```
ta                                                                  1622

<210> SEQ ID NO 2
<211> LENGTH: 2029
<212> TYPE: DNA
<213> ORGANISM: Mus musculus

<400> SEQUENCE: 2

tgaggcttct cagcttcaga tgcaagtgag tgggtgtctc acagagaagc aaagagaaga     60

gaacaggaga aaggtgtttc ccttgactgc ggaaacttta taaagaaaac ttagcttctc    120

tggagcagtc agcgtcagag ttctgtcctt gacacctgag tctcctccac aaggctgtga    180

gaaggaaacc ctttcctggg gctgggtgcc atgcagcagc ccatgaatta cccatgtccc    240

cagatcttct gggtagacag cagtgccact tcatcttggg ctcctccagg gtcagttttt    300

ccctgtccat cttgtgggcc tagagggccg gaccaaagga gaccgccacc tccaccacca    360

cctgtgtcac cactaccacc gccatcacaa ccactcccac tgccgccact gacccctcta    420

aagaagaagg accacaacac aaatctgtgg ctaccggtgg tatttttcat ggttctggtg    480

gctctggttg gaatgggatt aggaatgtat cagctcttcc acctgcagaa ggaactggca    540

gaactccgtg agttcaccaa ccaaagcctt aaagtatcat cttttgaaaa gcaaatagcc    600

aaccccagta caccctctga aaaaaaagag ccgaggagtg tggcccattt aacagggaac    660

ccccactcaa ggtccatccc tctggaatgg gaagacacat atggaaccgc tctgatctct    720

ggagtgaagt ataagaaagg tggccttgtg atcaacgaaa ctgggttgta cttcgtgtat    780

tccaaagtat acttccgggg tcagtcttgc aacaaccagc ccctaaacca caaggtctat    840

atgaggaact ctaagtatcc tgaggatctg gtgctaatgg aggagaagag gttgaactac    900

tgcactactg gacagatatg ggcccacagc agctacctgg gggcagtatt caatcttacc    960

agtgctgacc atttatatgt caacatatct caactctctc tgatcaattt tgaggaatct   1020

aagacctttt tcggcttgta taagctttaa aagaaaaagc attttaaaat gatctactat   1080

tctttatcat gggcaccagg aatattgtct tgaatgagag tcttcttaag acctattgag   1140

ccacaaagac cacaaggtcc aacaggtcag ctattaatta agactacatg agccacaaag   1200

acctcatgac cgcaaggtcc aacaggtcag ctatccttca ttttctcgag gtccatggag   1260

tggtccttaa tgcctgcatc atgagccaga tggaaggagg tctgtgactg agggacataa   1320

agctttgggc tgctgtgtga caatgcagag gcaaagagaa ggaactgtct gatgttaaat   1380

ggccaagagc attttagcca ttgaagaaaa aaacagagaa agaactgtct gatgttaaat   1440

ggccaagaga attttaacca ttgaagaaga cacctttaca ctcacttcca gggtgggtct   1500

acttactacc tcacagaggc cgtttttgag acatagttgt ggtatgaata tacaagggtg   1560

agaaaggagg ctcatttgac tgataagcta gagactgaaa aaaagacagt gtctcattgg   1620

caccatcttt actgttacct aatattttct gagccgacct ttgatcctaa cggagaagta   1680

agagggatgt ttgaggcaca aatcattctc tacatagcat gcatacctcc agtgcaatga   1740

tgtctgtgtg tttgtatgta tgagagcaaa cagattctaa ggagtcatat aaataaaata   1800

tgtacattat ggagtacata ttagaaacct gttacatttg atgctagata tctgaatgtt   1860

tcttggcaat aaactctaat agtcttcaaa atcttttatt atcagctact gatgctgttt   1920

ttctttaata caactagtat ttatgctctg aacatcctaa tgaggaaaag acaaataaaa   1980

ttatgttata gaatacagaa atgccttaag gacatagact ttggaaatc               2029
```

<210> SEQ ID NO 3
<211> LENGTH: 1023
<212> TYPE: DNA
<213> ORGANISM: Artificial Sequence
<220> FEATURE:
<223> OTHER INFORMATION: SB Transposase

<400> SEQUENCE: 3
atgggaaaat caaaagaaat cagccaagac ctcagaaaaa aaattgtaga cctccacaag 60
tctggttcat ccttgggagc aatttccaaa cgcctgaaag taccacgttc atctgtacaa 120
acaatagtac gcaagtataa acaccatggg accacgcagc cgtcataccg ctcaggaagg 180
agacgcgttc tgtctcctag agatgaacgt actttggtgc gaaaagtgca aatcaatccc 240
agaacaacag caaaggacct tgtgaagatg ctggaggaaa caggtacaaa agtatctata 300
tccacagtaa aacgagtcct atatcgacat aacctgaaag gccgctcagc aaggaagaag 360
ccactgctcc aaaaccgaca taagaaagcc agactacggt ttgcaactgc acatggggac 420
aaagatcgta ctttttggag aaatgtcctc tggtctgatg aaacaaaaat agaactgttt 480
ggccataatg accatcgtta tgtttggagg aagaaggggg aggcttgcaa gccgaagaac 540
accatcccaa ccgtgaagca cgggggtggc agcatcatgt tgtgggggtg ctttgctgca 600
ggagggactg gtgcacttca caaaatagat ggcatcatga ggaaggaaaa ttatgtggat 660
atattgaagc aacatctcaa gacatcagtc aggaagttaa agcttggtcg caaatgggtc 720
ttccaaatgg acaatgaccc caagcatact tccaaagttg tggcaaaatg gcttaaggac 780
aacaaagtca aggtattgga gtggccatca caaagccctg acctcaatcc tatagaaaat 840
ttgtgggcag aactgaaaaa gcgtgtgcga gcaaggaggc ctacaaacct gactcagtta 900
caccagctct gtcaggagga atgggccaaa attcacccaa cttattgtgg gaagcttgtg 960
gaaggctacc cgaaacgttt gacccaagtt aaacaattta aaggcaatgc taccaaatac 1020
tag 1023

<210> SEQ ID NO 4
<211> LENGTH: 229
<212> TYPE: DNA
<213> ORGANISM: Artificial Sequence
<220> FEATURE:
<223> OTHER INFORMATION: SB 5' ITR

<400> SEQUENCE: 4
cagttgaagt cggaagttta catacactta agttggagtc attaaaactc gtttttcaac 60
tactccacaa atttcttgtt aacaaacaat agttttggca agtcagttag gacatctact 120
ttgtgcatga cacaagtcat ttttccaaca attgtttaca gacagattat ttcacttata 180
attcactgta tcacaattcc agtgggtcag aagtttacat acactaagt 229

<210> SEQ ID NO 5
<211> LENGTH: 229
<212> TYPE: DNA
<213> ORGANISM: Artificial Sequence
<220> FEATURE:
<223> OTHER INFORMATION: SB 3' ITR

<400> SEQUENCE: 5
attgagtgta tgtaaacttc tgacccactg ggaatgtgat gaaagaaata aaagctgaaa 60
tgaatcattc tctctactat tattctgata tttcacattc ttaaaataaa gtggtgatcc 120
taactgacct aagacaggga atttttacta ggattaaatg tcaggaattg tgaaaaagtg 180
agtttaaatg tatttggcta aggtgtatgt aaacttccga cttcaactg 229

<210> SEQ ID NO 6
<211> LENGTH: 1785
<212> TYPE: DNA
<213> ORGANISM: Artificial Sequence
<220> FEATURE:
<223> OTHER INFORMATION: PB Transposase

<400> SEQUENCE: 6
atgggtagtt ctttagacga tgagcatatc ctctctgctc ttctgcaaag cgatgacgag 60
cttgttggtg aggattctga cagtgaaata tcagatcacg taagtgaaga tgacgtccag 120
agcgatacag aagaagcgtt tatagatgag gtacatgaag tgcagccaac gtcaagcggt 180
agtgaaatat tagacgaaca aaatgttatt gaacaaccag gttcttcatt ggcttctaac 240
agaatcttga ccttgccaca gaggactatt agaggtaaga ataaacattg ttggtcaact 300
tcaaagtcca cgaggcgtag ccgagtctct gcactgaaca ttgtcagatc tcaaagaggt 360
ccgacgcgta tgtgccgcaa tatatatgac ccacttttat gcttcaaact attttttact 420
gatgagataa tttcggaaat tgtaaaatgg acaaatgctg agatatcatt gaaacgtcgg 480
gaatctatga caggtgctac atttcgtgac acgaatgaag atgaaatcta tgctttcttt 540
ggtattctgg taatgacagc agtgagaaaa gataaccaca tgtccacaga tgacctcttt 600
gatcgatctt tgtcaatggt gtacgtctct gtaatgagtc gtgatcgttt tgattttttg 660
atacgatgtc ttagaatgga tgacaaaagt atacggccca cacttcgaga aaacgatgta 720
tttactcctg ttagaaaaat atgggatctc tttatccatc agtgcataca aaattacact 780
ccaggggctc atttgaccat agatgaacag ttacttggtt ttagaggacg gtgtccgttt 840
aggatgtata tcccaaacaa gccaagtaag tatggaataa aaatcctcat gatgtgtgac 900
agtggtacga agtatatgat aaatggaatg ccttatttgg gaagaggaac acagaccaac 960
ggagtaccac tcggtgaata ctacgtgaag gagttatcaa agcctgtgca cggtagttgt 1020
cgtaatatta cgtgtgacaa ttggttcacc tcaatccctt tggcaaaaaa cttactacaa 1080
gaaccgtata agttaaccat tgtgggaacc gtgcgatcaa acaaacgcga gataccggaa 1140
gtactgaaaa acagtcgctc caggccagtg ggaacatcga tgttttgttt tgacggaccc 1200
cttactctcg tctcatataa accgaagcca gctaagatgg tatacttatt atcatcttgt 1260
gatgaggatg cttctatcaa cgaaagtacc ggtaaaccgc aaatggttat gtattataat 1320
caaactaaag gcggagtgga cacgctagac caaatgtgtt ctgtgatgac ctgcagtagg 1380
aagacgaata ggtggcctat ggcattattg tacggaatga taaacattgc ctgcataaat 1440
tcttttatta tatacagcca taatgtcagt agcaagggag aaaaggttca aagtcgcaaa 1500
aaatttatga gaaaccttta catgagcctg acgtcatcgt ttatgcgtaa gcgtttagaa 1560
gctcctactt tgaagagata tttgcgcgat aatatctcta atattttgcc aaatgaagtg 1620
cctggtacat cagatgacag tactgaagag ccagtaatga aaaaacgtac ttactgtact 1680
tactgcccct ctaaaataag gcgaaaggca aatgcatcgt gcaaaaaatg caaaaaagtt 1740
atttgtcgag agcataaatat tgatatgtgc caaagttgtt tctga 1785

<210> SEQ ID NO 7
<211> LENGTH: 309
<212> TYPE: DNA
<213> ORGANISM: Artificial Sequence
<220> FEATURE:
<223> OTHER INFORMATION: PB 5' ITR

<400> SEQUENCE: 7

-continued ccctagaaag atagtctgcg taaaattgac gcatgcattc ttgaaatatt gctctctctt 60
tctaaatagc gcgaatccgt cgctgtgcat ttaggacatc tcagtcgccg cttggagctc 120
ccgtgaggcg tgcttgtcaa tgcggtaagt gtcactgatt ttgaactata acgaccgcgt 180
gagtcaaaat gacgcatgat tatcttttac gtgactttta agatttaact catacgataa 240
ttatattgtt atttcatgtt ctacttacgt gataacttat tatatatata ttttcttgtt 300
atagatatc 309

<210> SEQ ID NO 8
<211> LENGTH: 309
<212> TYPE: DNA
<213> ORGANISM: Artificial Sequence
<220> FEATURE:
<223> OTHER INFORMATION: PB 5' ITR

<400> SEQUENCE: 8
ccctagaaag atagtctgcg taaaattgac gcatgcattc ttgaaatatt gctctctctt 60
tctaaatagc gcgaatccgt cgctgtgcat ttaggacatc tcagtcgccg cttggagctc 120
ccgtgaggcg tgcttgtcaa tgcggtaagt gtcactgatt ttgaactata acgaccgcgt 180
gagtcaaaat gacgcatgat tatcttttac gtgactttta agatttaact catacgataa 240
ttatattgtt atttcatgtt ctacttacgt gataacttat tatatatata ttttcttgtt 300
atagatatc 309

<210> SEQ ID NO 9
<211> LENGTH: 238
<212> TYPE: DNA
<213> ORGANISM: Artificial Sequence
<220> FEATURE:
<223> OTHER INFORMATION: PB 3' ITR

<400> SEQUENCE: 9
taaaagtttt gttactttat agaagaaatt ttgagttttt gttttttttt aataaataaa 60
taaacataaa taaattgttt gttgaattta ttattagtat gtaagtgtaa atataataaa 120
acttaatatc tattcaaatt aataaataaa cctcgatata cagaccgata aaacacatgc 180
gtcaatttta cgcatgatta tctttaacgt acgtcacaat atgattatct ttctaggg 238